(12) United States Patent
Roche et al.

(10) Patent No.: US 12,702,458 B2
(45) **Date of Patent: *Aug. 11, 2026**

(54) ACROMION FRACTURE REPAIR SYSTEM

(71) Applicant: Advita Ortho, LLC, Gainesville, FL (US)

(72) Inventors: Christopher P. Roche, Gainesville, FL (US); Corey Gaydos, Gainesville, FL (US); Mark Bender, Gainesville, FL (US); David Koogle, Trenton, FL (US); George S. Athwal, London (CA); Joaquin Sanchez-Sotelo, Rochester, MN (US)

(73) Assignee: Advita Ortho, LLC, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/750,848

(22) Filed: Jun. 21, 2024

(65) Prior Publication Data

US 2024/0415554 A1 Dec. 19, 2024

Related U.S. Application Data

(63) Continuation of application No. 17/633,061, filed as application No. PCT/US2020/045206 on Aug. 6, 2020, now Pat. No. 12,016,601.

(Continued)

(51) Int. Cl.

*A61B 17/80* (2006.01)
*A61B 17/84* (2006.01)

(Continued)

(52) U.S. Cl.

CPC ...... *A61B 17/8061* (2013.01); *A61B 17/8004* (2013.01); *A61B 17/8085* (2013.01);

(Continued)

(58) Field of Classification Search

CPC .......... A61B 2017/681; A61B 17/8004; A61B 17/8064; A61B 17/8085; A61B 17/809; A61B 17/88

See application file for complete search history.

(56) References Cited

U.S. PATENT DOCUMENTS 9,072,557 B2 * 7/2015 Fierlbeck ............. A61B 17/809
9,358,053 B2 * 6/2016 Guy ....................... A61B 17/80

(Continued)

FOREIGN PATENT DOCUMENTS

CN 201987653 U 9/2011
CN 202568418 U 12/2012

(Continued)

OTHER PUBLICATIONS

European Search Report from European Patent Application No. 24201914.9 dated Oct. 16, 2024.

(Continued)

*Primary Examiner* — Larry E Waggle, Jr.
(74) *Attorney, Agent, or Firm* — GREENBERG TRAURIG, LLP

(57) ABSTRACT

A kit including (1) a plate configured to be secured to a scapular spine with a first end of the plate near a trigonum and a second end of the plate near an acromion; (2) a first hook including a mount, a first hook portion extending from the mount in a first direction, a spacer extending from the first hook portion in a transverse direction, and a second hook portion extending from an opposite end of the spacer in the first direction, the first hook adapted to extend around a lateral end of the acromion when fixed to the second end of the plate; and (3) a second hook including a mount, a curved portion curving away from the mount, and a hook (Continued)

portion at an opposite end of the curved portion, the second hook adapted to extend around the trigonum when fixed to the first end of the plate.

21 Claims, 18 Drawing Sheets

Related U.S. Application Data

(60) Provisional application No. 62/883,414, filed on Aug. 6, 2019.

(51) Int. Cl.
*A61B 17/88* (2006.01)
*A61B 17/56* (2006.01)
*A61B 17/68* (2006.01)

(52) U.S. Cl.
CPC .............. *A61B 17/84* (2013.01); *A61B 17/88* (2013.01); *A61B 2017/568* (2013.01); *A61B 2017/681* (2013.01)

(56) References Cited

U.S. PATENT DOCUMENTS 9,636,157 B2 5/2017 Medoff
9,775,657 B2 10/2017 Bernstein et al.
12,016,601 B2 * 6/2024 Roche .................... A61B 17/88
2009/0012569 A1 1/2009 Dall et al.
2013/0041375 A1 2/2013 Fierlbeck et al.

FOREIGN PATENT DOCUMENTS

| | | | | |
|---|---|---|---|---|
| CN | 103505279 | A | | 1/2014 |
| CN | 204274625 | U | | 4/2015 |
| CN | 204364103 | U | * | 6/2015 |
| CN | 206526100 | U | | 9/2017 |
| CN | 206526101 | U | | 9/2017 |
| CN | 107280751 | A | | 10/2017 |
| CN | 208274610 | U | | 12/2018 |
| EP | 1 743 586 | A1 | | 1/2017 |
| EP | 3 135 234 | A1 | | 3/2017 |
| JP | 2007-503885 | A | | 3/2007 |
| JP | 2014-514005 | A | | 6/2014 |
| JP | 2015-516221 | A | | 6/2015 |
| JP | 2017-524440 | A | | 8/2017 |
| JP | 2017-531939 | A | | 10/2017 |
| JP | 2019-69142 | A | | 5/2019 |
| TW | M537880 | U | | 9/2011 |
| WO | 97/18770 | A1 | | 5/1997 |
| WO | 2012/121830 | A1 | | 9/2012 |
| WO | 2018/026785 | A1 | | 2/2018 |
| WO | 2018/222449 | A1 | | 12/2018 |

OTHER PUBLICATIONS

International Search Report and Written Opinion from International Application No. PCT/US2020/045206 dated Dec. 18, 2020.

* cited by examiner 510
400
S
410

704
706
420
710
710
420
710
700
700
702

ACROMION FRACTURE REPAIR SYSTEM

CROSS-REFERENCE TO RELATED APPLICATION

This application is a continuation of U.S. patent application Ser. No. 17/633,061, filed Feb. 4, 2022, entitled "ACROMION FRACTURE REPAIR SYSTEM," which is a national phase filing under 35 USC 371 of International Application No. PCT/US2020/045206, filed Aug. 6, 2020, entitled "ACROMION FRACTURE REPAIR SYSTEM," which claims the benefit of U.S. Provisional Patent Application No. 62/883,414, filed Aug. 6, 2019, entitled "ACROMION FRACTURE REPAIR SYSTEM," the contents of which are incorporated herein by reference in their entirety.

FIELD OF THE INVENTION

The field of invention relates to devices for orthopedic use. More particularly, the field of invention relates to devices for use in the reconstruction of fatigue/insufficiency factures of the acromion and scapula that can occur after reverse total shoulder arthroplasty.

BACKGROUND OF THE INVENTION

Reverse total shoulder arthroplasty ("rTSA") is a surgical technique in which the shoulder's natural ball-and-socket joint, which has a rounded humeral head (i.e., ball) interfacing with the glenoid cavity (i.e., socket) of the scapula, is replaced by a reversed ball-and-socket joint, which has a glenosphere (i.e., ball) implanted on the shoulder and mating with a cup (i.e., socket) implanted on the humerus. Occasionally, fatigue/insufficiency fractures occur in the acromion and scapula after rTSA. Reconstruction of acromial and scapula fatigue/insufficiency fractures after rTSA is challenging and unsolved problem. These fracture types are not always able to be repaired; and healing after repair is not always reproducible for even the best shoulder specialists and traumatologists due to the highly variable anatomy which often consists of relatively thin bone with low vascularity. There is no ideal method of repair of acromial and scapular fatigue fractures and there are only a few currently available solutions for open reduction and internal fixation ("ORIF") surgery. When ORIF is used, shoulder specialists and traumatologists primarily utilize one or more straight/noncontoured plates with locking screws, compression screws, and/or a combination of each. Because of the highly variable scapular anatomy in terms of both size and shape/contour, few anatomically contoured plates are available and surgeons are often required to bend straight plates in order to get a better fit. Due to concerns of repair and healing, the most common method of treatment is immobilization of the patient's arm in a sling until the fracture heals. For both ORIF and immobilization, the rate of healing is unpredictable. FIG. 1A shows a representative radiographic depiction of a shoulder joint after rTSA and prior to scapular fracture, while FIG. 1B shows a representative radiographic depiction of the shoulder joint after scapular fracture following rTSA.

Recently, rTSA outcome studies have demonstrated that even if a fatigue/insufficiency fracture heals, the patient will not achieve the level of outcome and function that they experienced prior to the fracture. If the fracture fails to heal, the results are poor as the middle deltoid origin is on the acromion and the posterior deltoid origin is on the lateral acromion and scapular spine; without proper deltoid function, the reverse shoulder prosthesis fails to be able to generate a torque necessary for activities of daily living and joint stability is impaired.

Acromial and scapula fatigue/insufficiency fractures can occur any time after the initial rTSA procedure, occurring as early as the first day of surgery and as late as 10+ years after the surgical procedure. Acromial and scapula fatigue/insufficiency fractures after rTSA can occur at various locations on the acromion and scapular spine. These fracture types have been classified as type 1 (fracture of the lateral acromion with a deltoid avulsion), type 2 (fracture of the mid-scapular spine at-or around the location of the scapular notch), and type 3 (fracture at the base of the scapular spine). FIGS. 2A, 2B, and 2C show a superior view, a posterior view, and a superior-oblique view, respectively, of the portions of the acromion that fracture as a result of these different types of fractures. FIGS. 3A and 3B show a superior view and a posterior view, respectively, of a healthy scapula. FIGS. 3C and 3D show a superior view and a posterior view, respectively, of a scapula that has experienced a type 1 fracture. FIGS. 3E and 3F show a superior view and a posterior view, respectively, of a scapula that has experienced a type 2 fracture. FIGS. 3G and 3H show a superior view and a posterior view, respectively, of a scapula that has experienced a type 3 fracture. The rate of acromial and scapula fatigue/insufficiency fractures after rTSA is relatively low, but is typically reported to be between 1 and 10%. Type 2 fractures appear to be the most common scapular insufficiency fracture type after rTSA.

There are numerous potential causes of these acromial and scapular insufficiency/fatigue fractures. Some think that the fracture propagates from the tip glenoid plate screw into the scapular spine, while others postulate that the fractures occur due to overactivity or episodes of strenuous activity and/or trauma, and still others think that the fracture is caused by over-tensioning the deltoid and/or arm lengthening as a function of overstuffing the joint with too thick of an implant or too distal of an implant configuration for a given patient's anatomy. Still other thoughts include the use of biomechanically inefficient implants which have too small of a deltoid moment arm (resulting in too great of a deltoid force for arm elevation for a particular patient). There are also likely patient-specific anatomic/morphologic factors which predispose the patient to these types of insufficiency fractures, like a thin scapula/acromion, osteoporotic or osteopenic bone, the presence of an Os acromiale or a lesion which is associated with the CTA pathology, or perhaps a unique biomechanically detrimental anatomy such that there is insufficient acromial overhang or muscle mass, requiring the patient to produce abnormal physiologic loading during activities of daily loading. rTSA patients are associated with more scapular motion relative to non-rTSA patients, and it may be that the amount of scapular rotation influences this complication. The timing and level of rigor of the rehabilitation program may also play a role on the rate and severity of the acromial or scapular fatigue/insufficiency fracture. These fractures could also be caused during the surgery by traction with a retractor when attempting to gain exposure to the glenoid. Whatever the specific cause (or combination of causes), the patient population is predominantly female, osteoporotic, and elderly. As a result of these factors, the fracture is at a disadvantage for healing; patient health quality and patient co-morbidities also influence the quality of fracture reconstruction and the rate and probability of fracture healing over time.

The widespread and global usage of rTSA since its clearance in the US in 2003 and the lack of consensus solution to this complication type highlights the need for a better solution for acromial/scapular insufficiency fractures after rTSA, but also highlights the need for a solution if that fracture reconstruction fails, which it has been reported to at a relatively high rate due to patient factors and anatomic factors. For all these reasons, there is a need for a more effective solution to restore function and stability to the TSA patient after an acromial/scapular insufficiency fatigue fracture.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY OF THE INVENTION

Figures 1A, 1B:
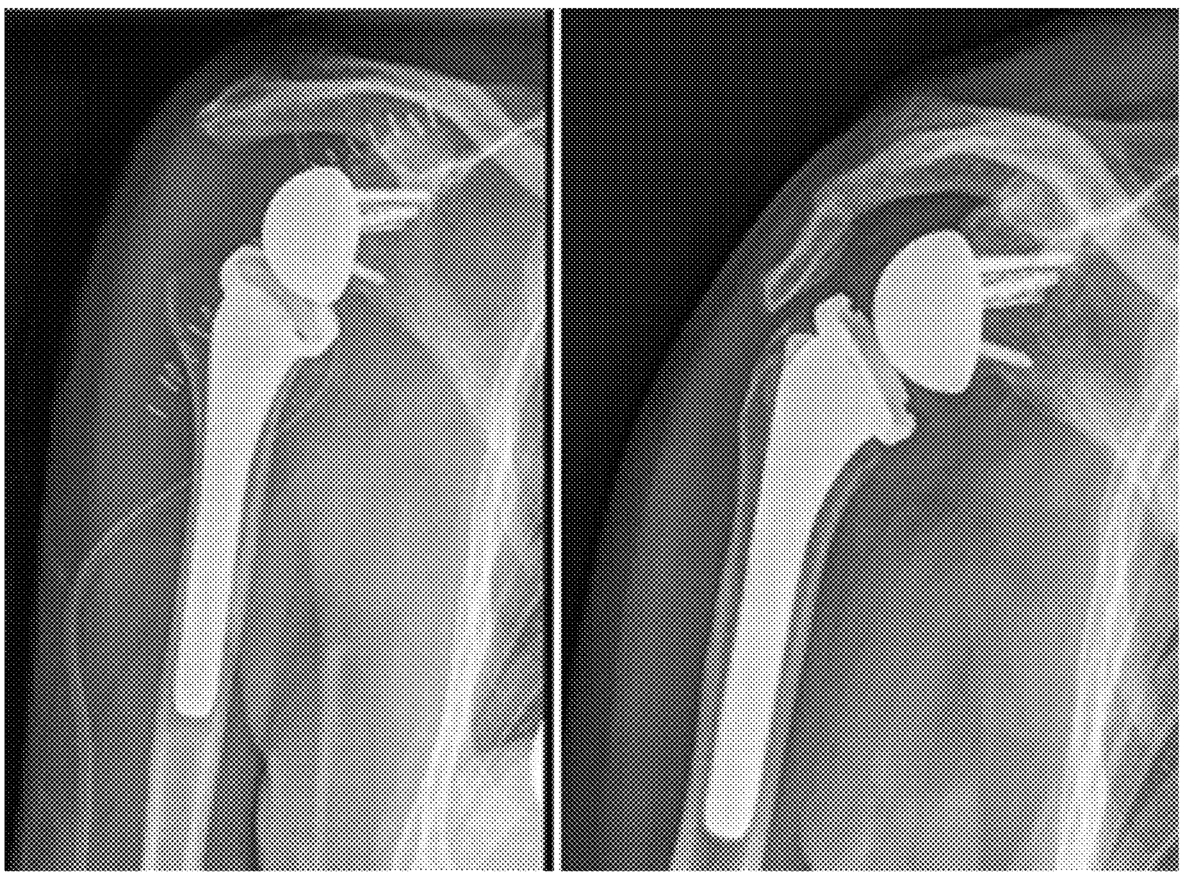
FIG. 1A shows an anterior-posterior radiographic view of a shoulder joint after rTSA and prior to scapular fracture.
FIG. 1B shows the rTSA shoulder joint of FIG. 1A after scapular fracture.
Figure 2A:
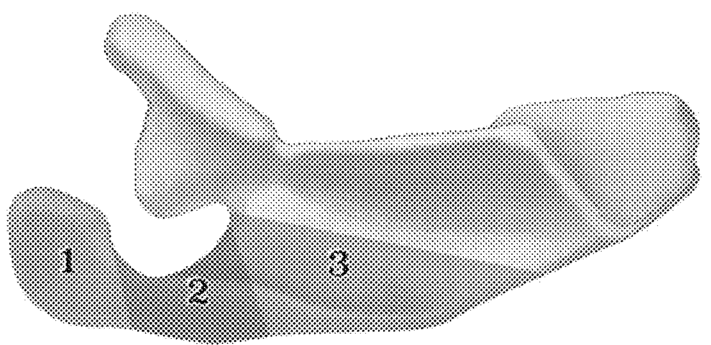
FIG. 2A shows a superior view of the locations of different scapular fractures.
Figure 2B:
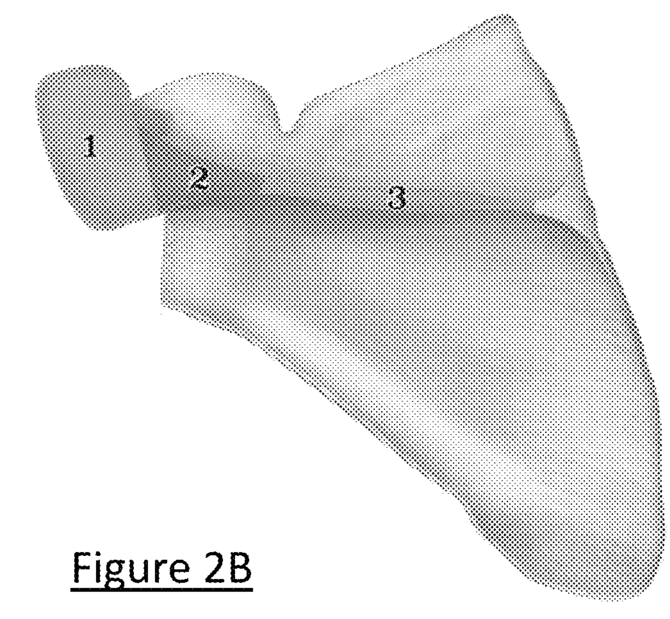
FIG. 2B shows a posterior view of the scapular fractures shown in FIG. 2A.
Figure 2C:
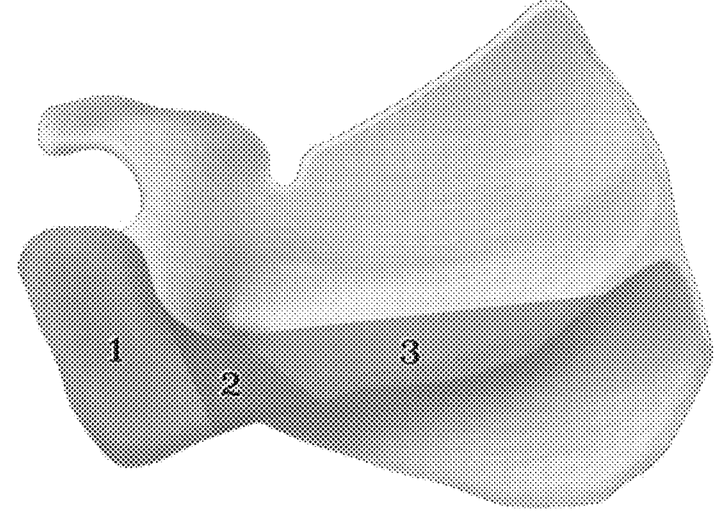
FIG. 2C shows a superior-oblique view of the scapular fractures shown in FIG. 2A.

The exemplary embodiments relate to devices for repair of acromial/scapular fractures. In some embodiments, the devices described herein are suitable for use to reconstruct the acromion and scapula of rTSA patients who have insufficiency fractures of the acromion or scapula.

In an embodiment, a scapula repair device includes a fracture fixation bone plate (referred to herein as a "plate" for brevity) having a first end, a second end opposite the first end, and at least one fixation point positioned along the plate between the first end and the second end; at least one hook, each of the at least one hook being mounted to a corresponding one of the at least one fixation point of the plate; and at least one fixation element, each of the at least one fixation element being positioned so as to secure a corresponding one of the at least one hook to the corresponding one of the at least one fixation point and to secure the plate to a scapula of a patient, wherein the plate is configured such that, when the plate is secured to the scapula of the patient, the plate extends along at least a portion of a scapular spine of the scapula and at least a portion of an acromion of the scapula, and wherein the plate and the at least one hook are configured such that, when the plate is secured to the scapula of the patient, the plate and the at least one hook cooperate to retain the acromion and/or the scapula in a desired position. In some embodiments, such retention of the acromion and/or the scapula is suitable to facilitate healing of a fracture, such as a fracture of one of the three different fracture types that occur after rTSA (e.g., as described above with reference to FIGS. 3A-3H).

In an embodiment, a kit includes at least one plate having a first end, a second end opposite the first end, and at least one fixation point positioned along the plate between the first end and the second end, wherein each at least one plate is configured such that, when the at least one plate is secured to a scapula of a patient, at least one the plate extends along at least a portion of a scapular spine of the scapula and at least a portion of an acromion of the spine; a plurality of hooks, each of the plurality of hooks being configured to be secured to a selected one of the at least one fixation point of a selected one of the at least one plate; a plurality of fixation elements, each of the fixation elements being configured to secure a selected one of the plurality of hooks to the selected one of the at least one fixation point of the selected one of the at least one plate and to secure the selected one of the at least one plate to the scapula of the patient, wherein each of the at least one plate and each of the at least one hook are configured such that, when a selected at least one of the at least one hook is secured to the selected one of the at least one plate and the selected one of the at least one plate is secured to the scapula of the patient, the selected one of the at least one plate and the selected at least one of the at least one hook cooperate to retain the acromion in a desired position.

In some embodiments, a kit includes at least one plate and a plurality of hooks, wherein each of the at least one plate includes a plurality of fixation points that are spaced apart along each of the at least one plate, wherein the at least one plate includes at least a first plate that is an elongate plate having a first end and a second end opposite the first end, wherein the first plate is sized and shaped so as to be configured to be positioned and to extend along a scapular spine of a scapula of a patient such that the first end is proximate to a trigonum of the scapula and the second end is proximate to an acromion of the scapula and configured to be secured to the scapular spine, wherein each of the hooks is configured to be fixed to a selected one of the fixation points of a selected one of the at least one plate, wherein the plurality of hooks includes at least a first hook including (1) a mount that is configured to be fixed to a selected one of the fixation points of a selected one of the at least one plate, (2) a first hook portion positioned proximate to the mount and extending away from the mount in a first direction, (3) a spacer portion extending away from the first hook portion in a transverse direction that is perpendicular to the first direction, and (4) a second hook portion extending from an end of the spacer portion that is opposite the first hook portion and extending in the first direction, wherein the first hook is sized and shaped so as to be configured so that the first and second hook portions extend around a lateral end of the acromion when the first hook is fixed to a first one of the fixation points of the first plate that is proximate to the second end of the plate, and a second hook including (1) a mount that is configured to be fixed to a selected one of the fixation points of a selected one of the at least one plate, (2) a curved portion extending away from and curving back toward the mount, and (3) a hook portion at an end of the curved portion that is opposite the mount of the second hook, wherein the second hook is sized and shaped to be configured so that the hook portion of the second hook extends around the trigonum of the scapula when the second hook is fixed to a second one of the fixation points of the first plate that is proximate to the first end of the first plate.

In some embodiments, the first plate is contoured so as to conform to the scapular spine.

In some embodiments, at least one of the at least one plate is conformable so as to allow a user to conform the plate to a portion of the scapula.

In some embodiments, the hook portion of the second hook is Y-shaped.

In some embodiments, the first plate, the first hook, and the second hook are configured to cooperate to apply a compression force to a fracture along the scapular spine when (a) the first plate is secured to the scapular spine, (b) the first hook is fixed to the first one of the fixation points of the first plate and positioned such that the first and second hook portions of the first hook extend around the lateral end of the acromion, and (c) the second hook is fixed to the second one of the fixation points of the first plate and positioned such that the hook portion of the second hook extend around the trigonum of the scapula.

In some embodiments, a kit also includes at least one fastener configured to be secured to one of the fixation points of one of the at least one plate the plate and to the scapula so as to secure the one of the at least one plate to the scapula.

In some embodiments, a kit also includes at least one fastener configured to be secured to one of the fixation points of one of the at least one plate and to a selected one of the plurality of hooks so as to secure the selected one of the plurality of hooks to the one of the at least one plate.

In some embodiments, the at least one plate also includes a second plate, wherein the second plate has a first end and a second end opposite the first end of the second plate, wherein the second plate is a curved plate that is sized and shaped so as to be configured to be positioned adjacent to the scapular spine of the patient and the acromion of the patient such that the first end of the second plate is positioned proximate to the trigonum of the patient and the plate extends along the scapular spine of the patient and the acromion of the patient to the second end that is positioned proximate to a top of the acromion of the patient.

In some embodiments, the second hook is sized and shaped so as to be configured so that the hook portion of the second hook extends around the top of the acromion of the patient when the second hook is fixed to one of the fixation points of the second plate that is located proximate to the second end of the second plate.

In some embodiments, the at least one plate includes a second plate that is an elongate plate having a first end and a second end opposite the first end of the second plate, wherein the second plate is sized and shaped so as to be configured to be positioned along the scapular spine and to extend along the scapular spine from the first end that is positioned along an inferior surface of the scapular spine to the second end that is positioned on a posterior surface of the acromion. In some embodiments, the plurality of hooks includes a third hook including (1) a mount that is configured to be fixed to a selected one of the fixation points of a selected one of the at least one plate, (2) a curved portion extending away from and curving back toward the mount, and (3) a hook portion at an end of the curved portion that is opposite the mount of the second hook, and (4) a fixation hole extending through the hook portion, wherein the fixation hole is configured to receive a fastener so as to fix the hook portion to the scapula. In some embodiments, the third hook is sized and shaped so as to be configured so that the hook portion extends over a superior surface of the scapular spine when the second plate is positioned along the scapular spine and the second hook is fixed to one of the fixation points of the second plate that is positioned along the inferior surface of the scapular spine. In some embodiments, the kit also includes a fastener that is configured to be secured in both the mount and the fixation hole of the third hook. In some embodiments, the fastener is configured to extend through the mount, the scapular spine, and the fixation hole of the third hook when (a) the second plate is positioned along the scapular spine and (b) the third hook is fixed to the one of the fixation points of the second plate that is positioned along the inferior surface of the scapular spine such that the hook portion of the third hook extends over the superior surface of the scapular spine.

In some embodiments, a method includes (1) providing a kit including at least one plate, a plurality of hooks, and a plurality of fasteners; wherein each of the at least one plate includes a plurality of fixation points that are spaced apart along each of the at least one plate, wherein the at least one plate includes at least a first plate that is an elongate plate having a first end and a second end opposite the first end, wherein the first plate is sized and shaped so as to be configured to be positioned and to extend along a scapular spine of a scapula of a patient such that the first end is proximate to a trigonum of the scapula and the second end is proximate to an acromion of the scapula and configured to be secured to the scapular spine, and wherein each of the hooks is configured to be fixed to a selected one of the fixation points of a selected one of the at least one plate, wherein a first hook of the plurality of hooks includes (a) a mount that is configured to be fixed to a selected one of the fixation points of a selected one of the at least one plate, (b) a first hook portion positioned proximate to the mount and extending away from the mount in a first direction, (c) a spacer portion extending away from the first hook portion in a transverse direction that is perpendicular to the first direction, and (d) a second hook portion extending from an end of the spacer portion that is opposite the first hook portion and extending in the first direction, wherein the first hook is sized and shaped so as to be configured so that the first and second hook portions extend around a lateral end of the acromion when the first hook is fixed to a first one of the fixation points of the first plate that is proximate to the second end of the plate, and wherein a second hook of the plurality of hooks includes (a) a mount that is configured to be fixed to a selected one of the fixation points of a selected one of the at least one plate, (b) a curved portion extending away from and curving back toward the mount, and (c) a hook portion at an end of the curved portion that is opposite the mount of the second hook, wherein the second hook is sized and shaped so as to be configured so that the hook portion of the second hook extends around the trigonum of the scapula when the second hook is fixed to a second one of the fixation points of the first plate that is proximate to the first end of the first plate; (2) fixing the first hook to the first one of the fixation points of the first plate with a first one of the plurality of fasteners; (3) fixing the second hook to the second one of the fixation points of the first plate with a second one of the plurality of fasteners; (4) positioning the first plate along a scapular spine of a scapula of a patient such that the first end is proximate to a trigonum of the scapula and the second end is proximate to an acromion of the scapula; and (5) fastening the first plate, the first hook, and the second hook to the scapular spine with at least a third one of the plurality of fasteners such that the first hook extends around a lateral end of the acromion, such that the second hook extends around the trigonum, and such that the first plate, the first hook, and the second hook cooperate to apply a compression force along the scapular spine.

DETAILED DESCRIPTION OF THE INVENTION

The exemplary embodiments relate to a fracture fixation system for patients with acromial and scapular fractures after rTSA. In some embodiments, an exemplary fracture fixation system restores stability to the shoulder with a fractured acromion and/or scapula through use of a scapular plating system including at least one modular hook that secures around at least one corresponding anatomic scapular feature (e.g., the acromion, the scapular spine, or the scapular trigonum). In some embodiments, at least one hook is monolithic with a plate (e.g., integrally formed from a single piece of a plate material). In some embodiments, at least one hook is modularly secured to a plate with a mechanical locking mechanism. In some embodiments, the plate construct (e.g., a plate including at least one integrally formed hook, a plate including at least one modularly attached hook, etc.) can be secured to the scapula with the aid of screws, sutures, wire, and/or pins.

In some embodiments, a plate that is used in connection with at least one modular hook facilitates a simpler surgical technique through a smaller incision while also improving the availability to account for multiple various anatomic size ranges (e.g., by providing modular hooks of various shapes and sizes) to account for the variable scapular anatomy/morphology, thereby reducing the overall scope and kit cost required to account for the anatomical variability required for the global marketplace. In some embodiments, a plate that is used in connection with at least one modular hook simplifies the manufacturing process and requires lower cost for all the implants in the kit (e.g., by enabling mixing and matching of different configurations).

In some embodiments, a plate that is used in connection with at least one modular hook is able to be placed at morphologically/anatomically strategic locations on a bone, tailored to each patient's individual fracture type (e.g., Type 1, 2, or 3). For example, such modular hooks can be placed on the lateral acromion (see, e.g., FIGS. 5E and 5F) or directed toward the medial portion of the acromion. FIGS. 5E and 5F also show these holes secured along the medial scapular border, at or around the scapular trigonum. Similarly, modular hooks can be placed along the anterior portion of the acromion (see, e.g., FIGS. 6E and 6F) or instead directed toward the posterior portion of the acromion if the orthopedic surgeon/traumatologist deems that location to facilitate the best reconstruction. Similarly, the plate and modular hooks can be secured to the scapular spine, either above the scapular spine, below the scapular spine, or along the side of the scapular spine (see, e.g., FIGS. 7A-7F). In some embodiments, for even more compounded morphological variability or to better support complex fracture comminution, the plate itself is also modular (see, e.g., FIGS. 8A-8E) and can also be used in connection with modular hooks. In some embodiments, such a modular connection can have angular/tilt variability and also variability in rotation and position.

In some embodiments, holes for screw fixation can be positioned at different locations and orientations on the plate to facilitate reconstruction and compression across the fracture lines and the impart additional stability for each of the different fracture types. In some embodiments, these modular hooks can also accept screws for added fixation (see, e.g., FIGS. 4C and 4D). Additionally, in some embodiments, numerous holes of various sizes for sutures and wires can be designed to facilitate the reconstruction. In some embodiments, the sizes of such holes are selected to allow needles of various sizes to easily pass therethrough with the plate compressed against the bone. In some embodiments the edges of the suture holes are configured to not abrade a suture when the suture is secured against the plate.

In some embodiments, exemplary plates and modular hooks are provided in multiple different sizes and shapes to account for the various acromion and scapula fracture types that the orthopedic surgeon may be presented with after rTSA, namely: type 1, type 2, and type 3 scapular fractures as discussed above. The figures accompanying the exemplary embodiments depict multiple views of different design variations of the proposed device to account for the different possible locations of fractures. For example, as depicted in FIGS. 5E, 5F, 6E, 6F, 7E, and 7F, for a type 1 or type 2 fracture, a modular hook may be placed laterally on the acromion, along or around different regions of the acromion, and/or at a different location (e.g., posteriorly, anteriorly, or medially on the scapula, etc.). Conversely, for a type 2 or type 3 fracture as depicted in FIGS. 5E, 5F, 7E, and 7F, a modular hook may be placed over or under the scapular spine, medially on the scapula at or around the scapular trigonum, and/or at a different location (e.g., posteriorly, anteriorly, or medially on the scapula, etc.).

In some embodiments, exemplary plates and modular hooks are provided in multiple different shapes and sizes for each fracture type and are provided in a range of sizes and shapes to account for the normal anatomic variation of the different anatomic morphology of the acromion and scapular spine. For example, as depicted in FIGS. 5B-5D and 6C-6F, a n exemplary plate and modular hook may be configured to secure to the top of the scapular spine and acromion and then rotate to the side or undersurface of the scapular spine for additional multi-planar support. Conversely, as depicted in FIGS. 7C-7F, an exemplary plate may be placed superiorly on the scapular spine and may rotate to the undersurface of the acromion. In some embodiments, different extensions and shapes are configured or modularly attached to provide multiple various options and positions for screw/suture/wire fixation into the scapula and to gain greater fixation between the bone fragments.

Figure 4A:
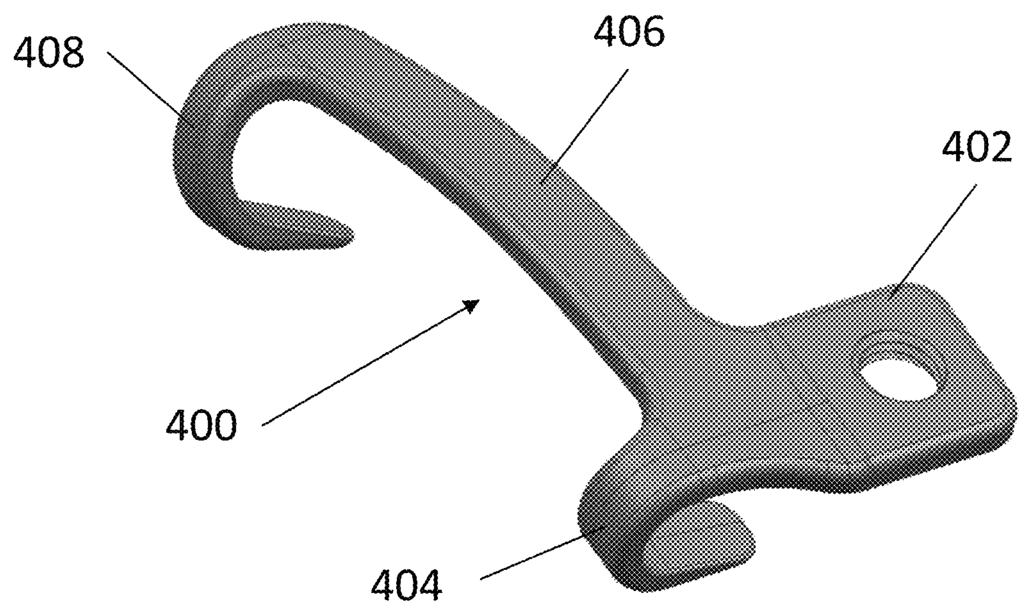
FIG. 4A shows a first exemplary modular hook.

FIG. 4A shows a perspective view of a first exemplary hook 400 that may form part of an exemplary acromion/scapula fracture repair system. In some embodiments, the hook 400 is sized and shaped for fixation adjacent the lateral acromion. In some embodiments, the hook 400 includes a mount 402 that is configured to mount the hook 400 to a plate, a first hook portion 404 proximate the mount 402, a spacer portion 406 extending away from the first hook portion 404, and a second hook portion 408 at the end of the spacer portion 406 opposite the first hook portion 404.

Figure 4B:
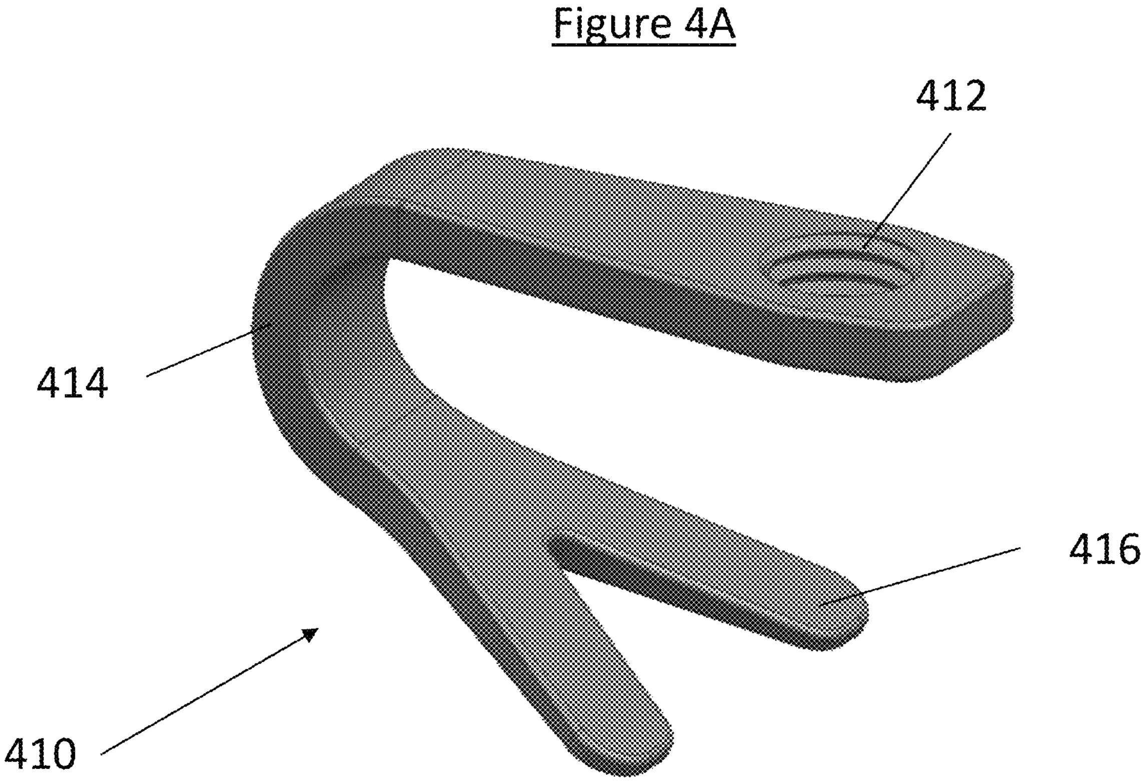
FIG. 4B shows a second exemplary modular hook.

FIG. 4B shows a perspective view of a second exemplary hook 410 that may form part of an exemplary acromion/scapula fracture repair system. In some embodiments, the hook 410 is sized and shaped for fixation adjacent the medial scapular blade near the trigonum. In some embodiments, the hook 410 is sized and shaped for fixation at the top of the acromion. In some embodiments, the hook 410 includes a mount 412 that is configured to mount the hook 410 to a plate, a curved portion 414 extending away from and curving back toward the mount 412, and a y-shaped hook portion 416 at the end of the curved portion 414 opposite the mount 412.

Figures 4C, 4D:
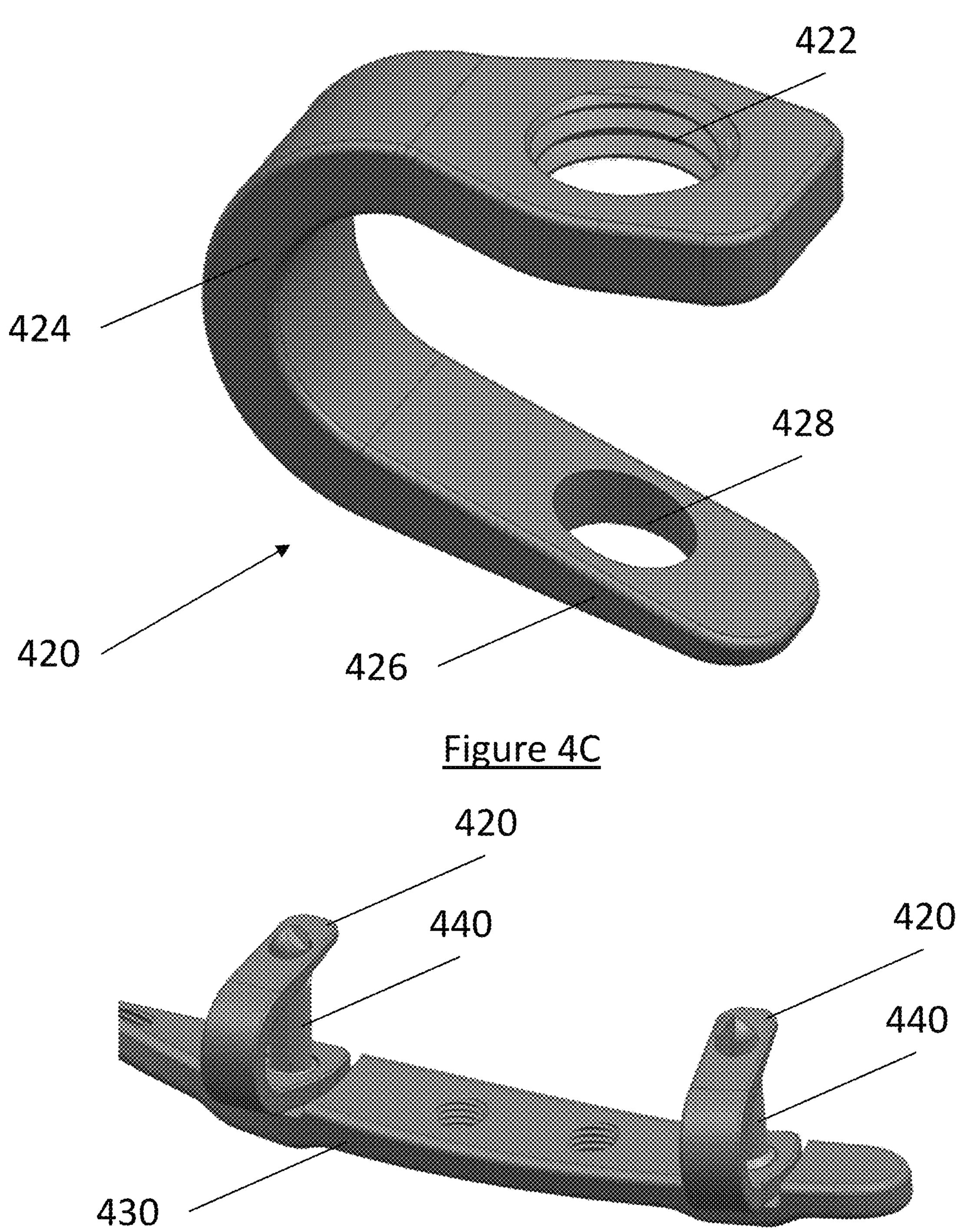
FIG. 4C shows a third exemplary modular hook.
FIG. 4D shows two of the third exemplary modular hook of FIG. 4C as attached to an exemplary base.

FIG. 4C shows a perspective view of a third exemplary hook 420 that may form part of an exemplary acromion/scapula fracture repair system. In some embodiments, the hook 420 is sized and shaped for fixation along the scapular spine. In some embodiments, the hook 420 includes a mount 422 that is configured to mount the hook 420 to a plate, a curved portion 424 extending away from and curving back toward the mount 422, a hook portion 426 at the end of the curved portion 424 opposite the mount 422, and a fixation hole 428 extending through the hook portion 426 and configured to receive an attachment element (e.g., a screw) extending therethrough to provide improved fixation. FIG. 4D shows a perspective view of a portion of an exemplary plate 430 and two of the third exemplary hook 420. As shown in FIG. 4D, in some embodiments, for each of the exemplary hook 420, a screw 440 secures the exemplary hook 420 to the plate 430 by installation through a hole 432 of the plate 430, the mount 422 of the hook 420, and the fixation hole 428 of the hook 420.

Figure 5A:
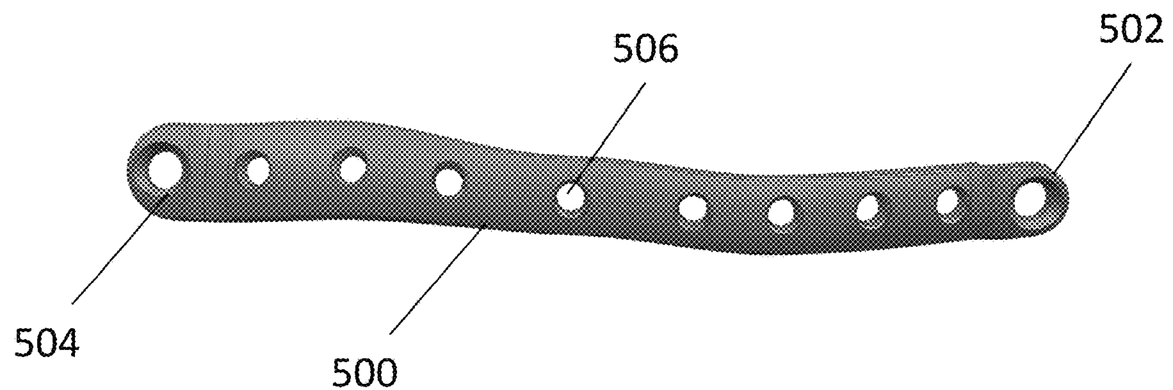
FIG. 5A shows a first exemplary plate.
Figure 5B:
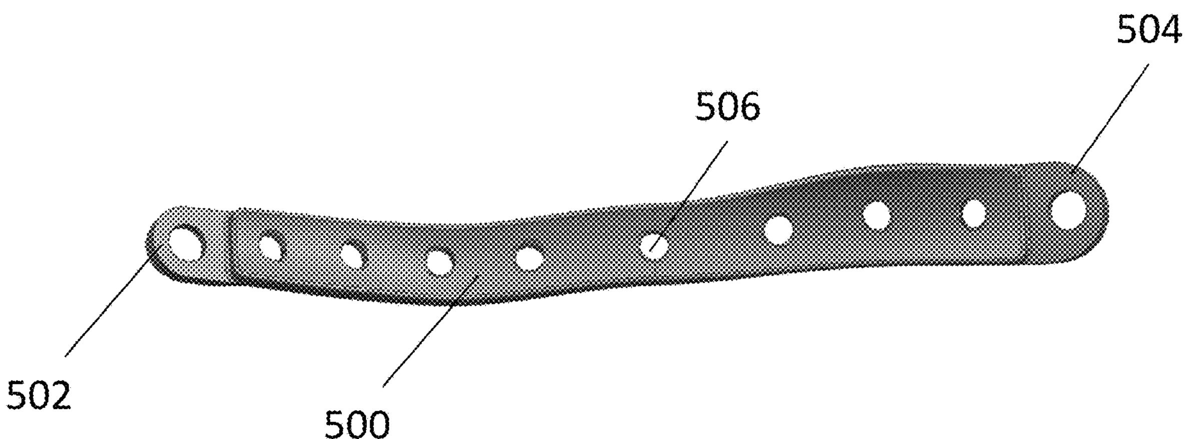
FIG. 5B shows a reverse view of the first exemplary plate of FIG. 5A.

FIGS. 5A and 5B shows perspective views of a first exemplary plate 500. In some embodiments, the plate 500 is sized and shaped to be positioned along a scapular spine of a patient. In some embodiments, the plate 500 includes a first end 502 (e.g., a medial end) and a second end 504 (e.g., a lateral end). In some embodiments, the plate 500 includes a plurality of fixation points 506 (e.g., holes) extending therethrough and configured to facilitate securing the plate 500 to a bone by mechanical securing devices such as screws, sutures, wire, pins, etc. In the embodiment of the plate 500 shown in FIGS. 5A and 5B, the plate 500 includes ten (10) of the fixation points 506, but it will be apparent to those of skill in the art that this quantity is only exemplary and that the plate 500 may include any number of the fixation points 506.

Figure 5C:
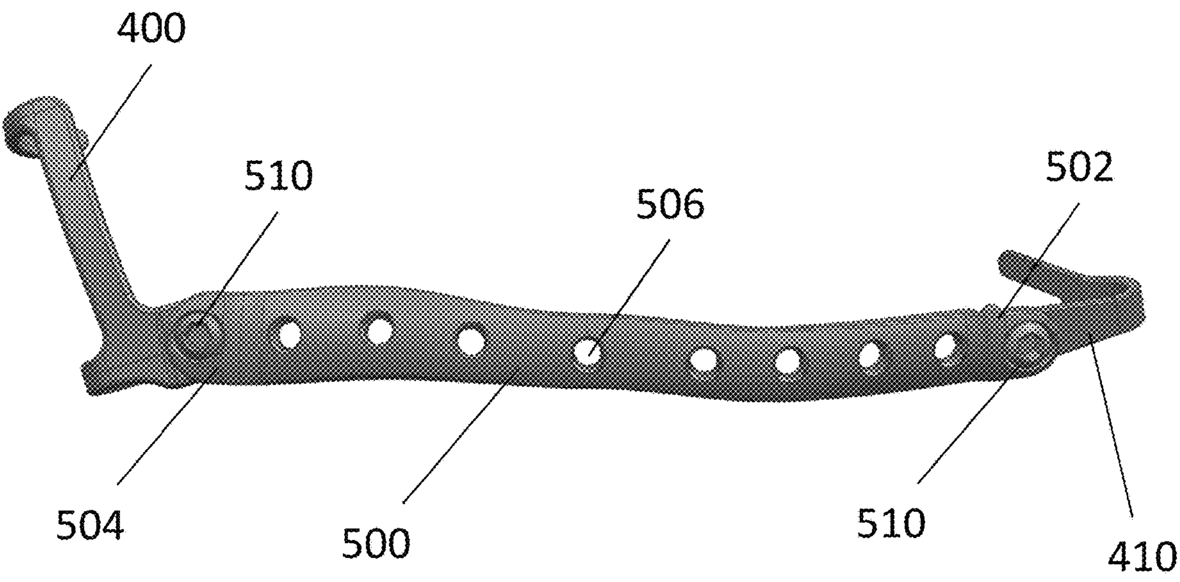
FIG. 5C shows the first exemplary plate of FIG. 5A as configured with exemplary hooks.
Figure 5D:
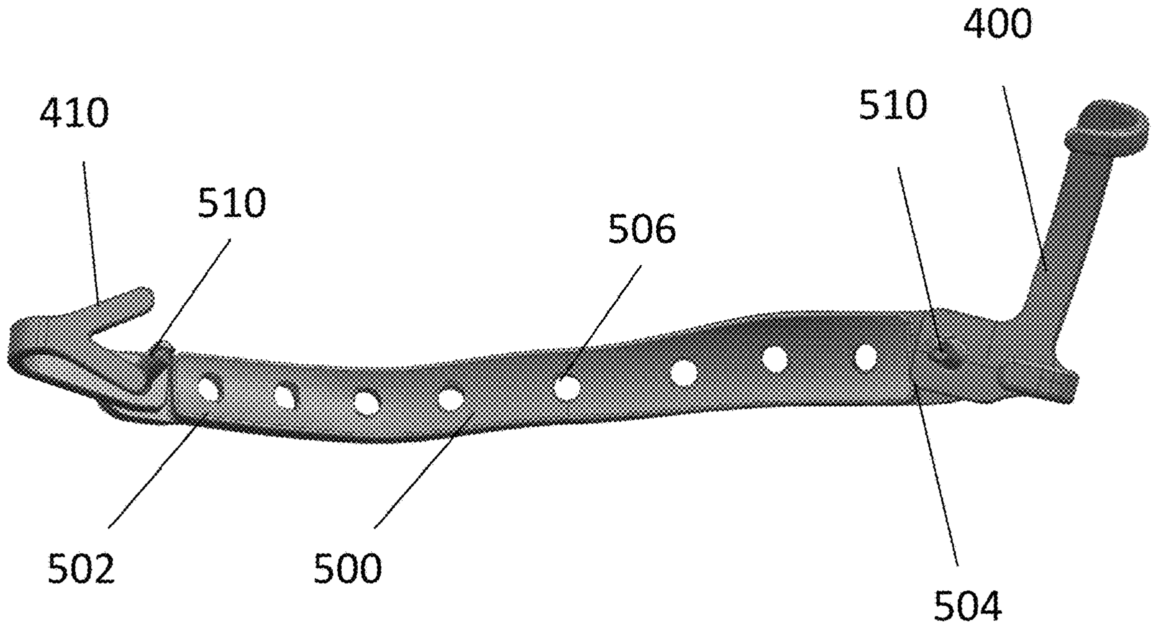
FIG. 5D shows a reverse view of the exemplary plate and exemplary hooks of FIG. 5C.
Figures 5E, 5F:
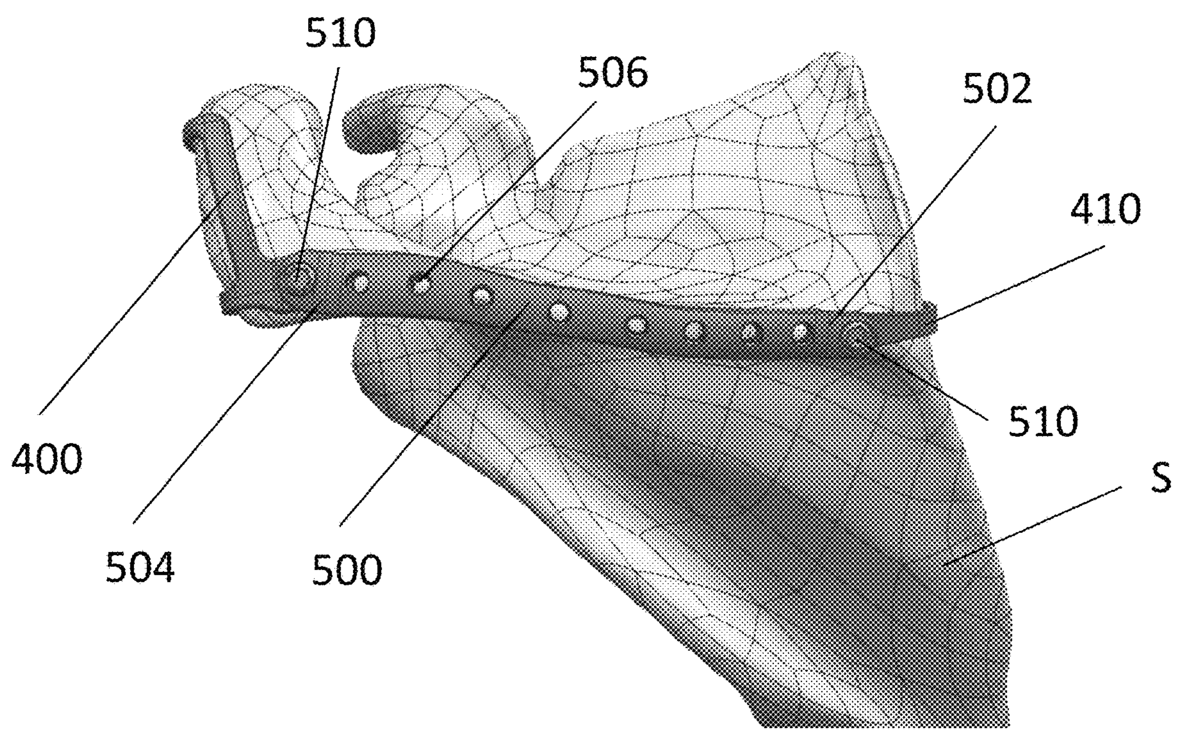
FIG. 5E shows the first exemplary plate and exemplary hooks of FIG. 5C as secured to a representative scapula.
FIG. 5F shows an alternate view of the first exemplary plate and exemplary hooks and representative scapula of FIG. 5D.

FIGS. 5C and 5D shows a perspective view of the plate 500 as prepared for securing to a scapula of a patient. As shown in FIGS. 5C and 5D, the plate 500 has been prepared by securing one of the second exemplary hook 410 to the first end 502 and by securing one of the first exemplary hook 400 to the second end 504. In some embodiments, as shown in FIGS. 5C and 5D, the first exemplary hook 400 and the second exemplary hook 410 are secured to the plate 500 by screws 510. The combination of the plate 500, the first exemplary hook 400, the second exemplary hook 410, and the screws 510 is referred to herein as a construct 520.

FIGS. 5E and 5F show perspective views of a representative scapula S, with the construct 520 secured thereto. FIG. 5E shows a posterior view and FIG. 5F shows an anterior view. As shown in FIGS. 5E and 5F, the second exemplary hook 410 extends around the medial scapular blade near the trigonum, the plate 500 extends along the scapular spine, and the first exemplary hook 400 extends around the lateral acromion. In some embodiments, the screws 510 extend into the scapula to secure the construct 520 thereto. In some embodiments, the first exemplary hook 400, the plate 500, the second exemplary hook 410, and the screws 510 cooperate to retain the acromion in a desired (e.g., anatomically correct) position.

Figure 6A:
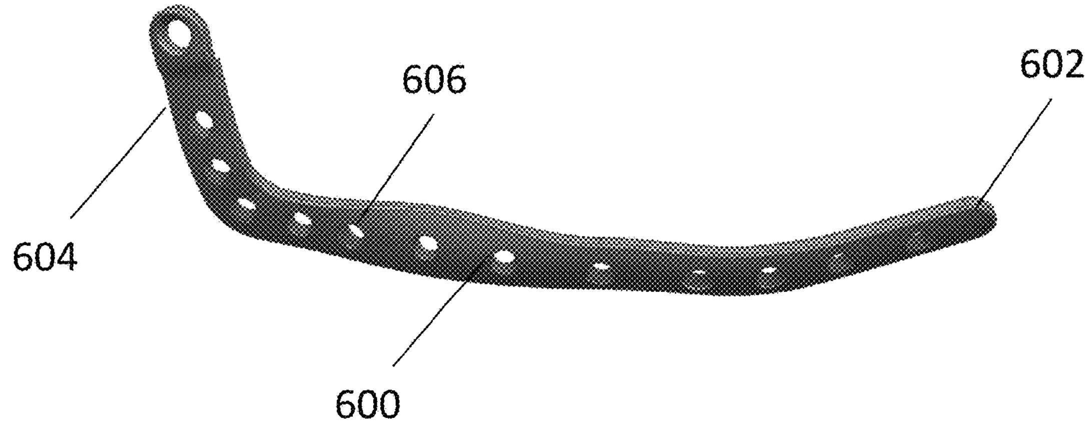
FIG. 6A shows a perspective view of a second exemplary plate.
Figure 6B:
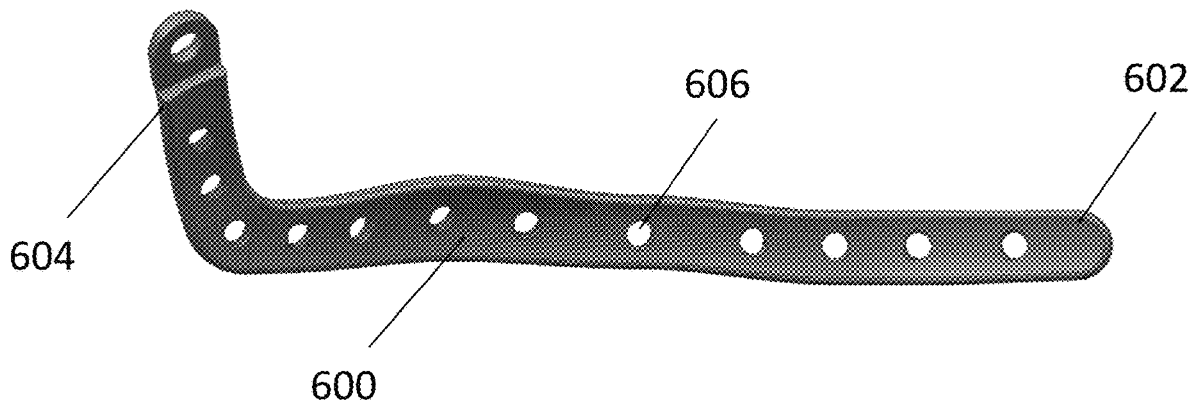
FIG. 6B shows a reverse perspective view of the second exemplary plate of FIG. 6A.

FIGS. 6A and 6B show perspective views of a second exemplary plate 600. In some embodiments, the plate 600 is sized, shaped, and curved to extend along a scapular spine and an acromion of a patient. In some embodiments, the plate 600 includes a first end 602 (e.g., a medial end) and a second end 604 (e.g., a lateral end). In some embodiments, the plate 600 includes a plurality of fixation points 606 (e.g., holes) extending therethrough and configured to facilitate securing the plate 600 to a bone by mechanical securing devices such as screws, sutures, wire, pins, etc. In the embodiment of the plate 600 shown in FIGS. 6A and 6B, the plate 600 includes thirteen (13) of the fixation points 606, but it will be apparent to those of skill in the art that this quantity is only exemplary and that the plate 600 may include any number of the fixation points 606.

Figure 6C:
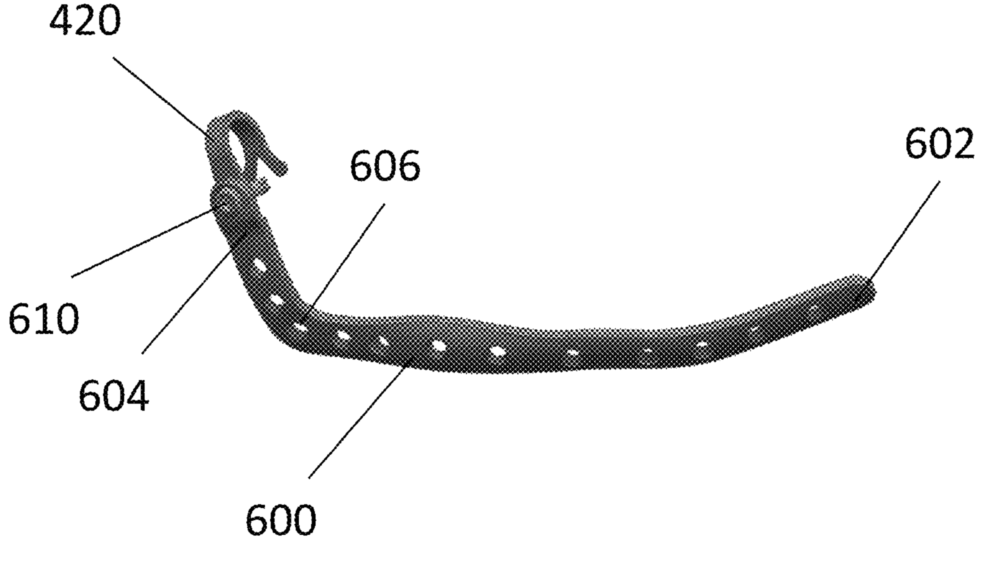
FIG. 6C shows the second exemplary plate of FIG. 6A as configured with an exemplary hook.
Figure 6D:
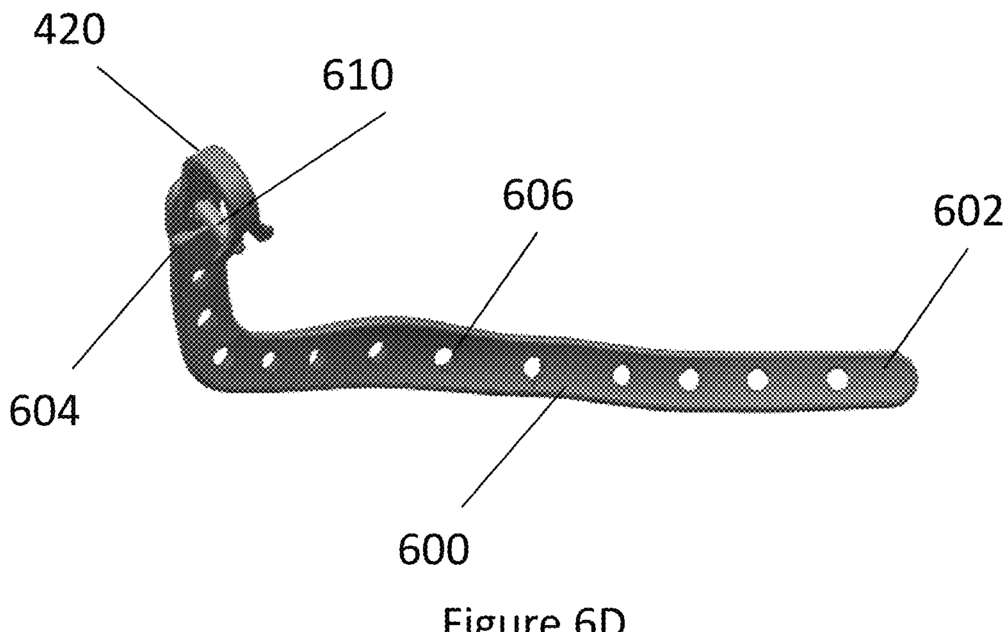
FIG. 6D shows an alternate view of the second exemplary plate and exemplary hook of FIG. 6C.

FIGS. 6C and 6D show perspective views of the plate 600 as prepared for securing to a scapula of a patient. FIG. 6C shows a posterior perspective view and FIG. 6D shows an anterior perspective view. As shown in FIGS. 6C and 6D, the plate 600 has been prepared by securing one of the third exemplary hook 420 to the second end 604. In some embodiments, as shown in FIGS. 6C and 6D, the third exemplary hook 420 is secured to the plate 600 by a screw 610. The combination of the plate 600, the third exemplary hook 420, and the screw 610 is referred to herein as a construct 620.

Figure 6E:
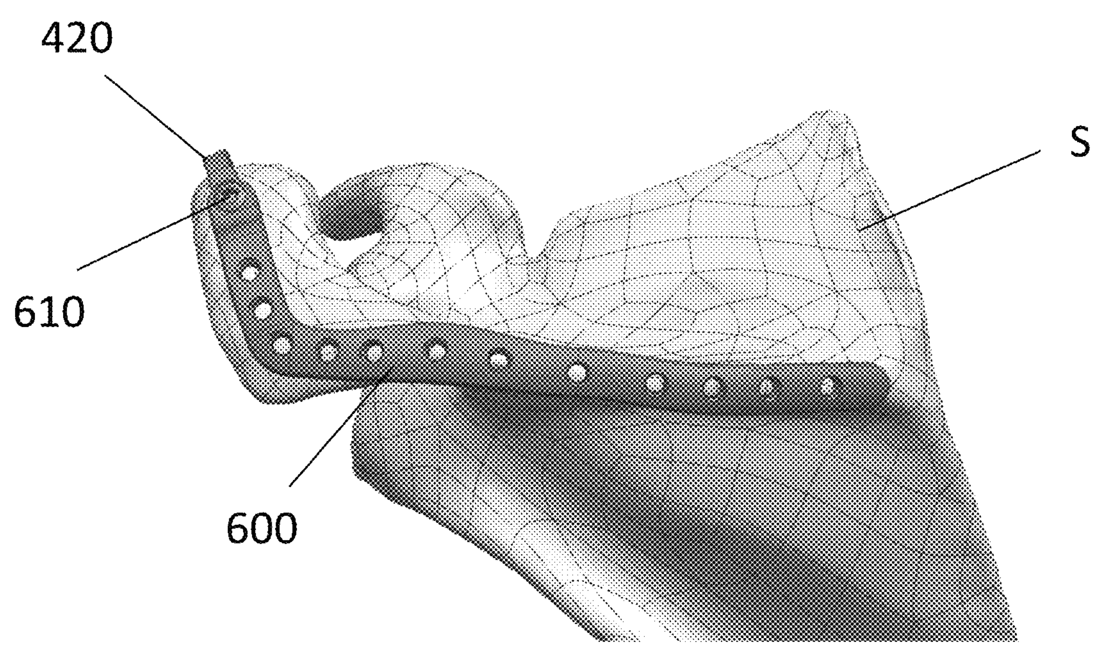
FIG. 6E shows the second exemplary plate and exemplary hook of FIGS. 6C and 6D as secured to a representative scapula.
Figure 6F:
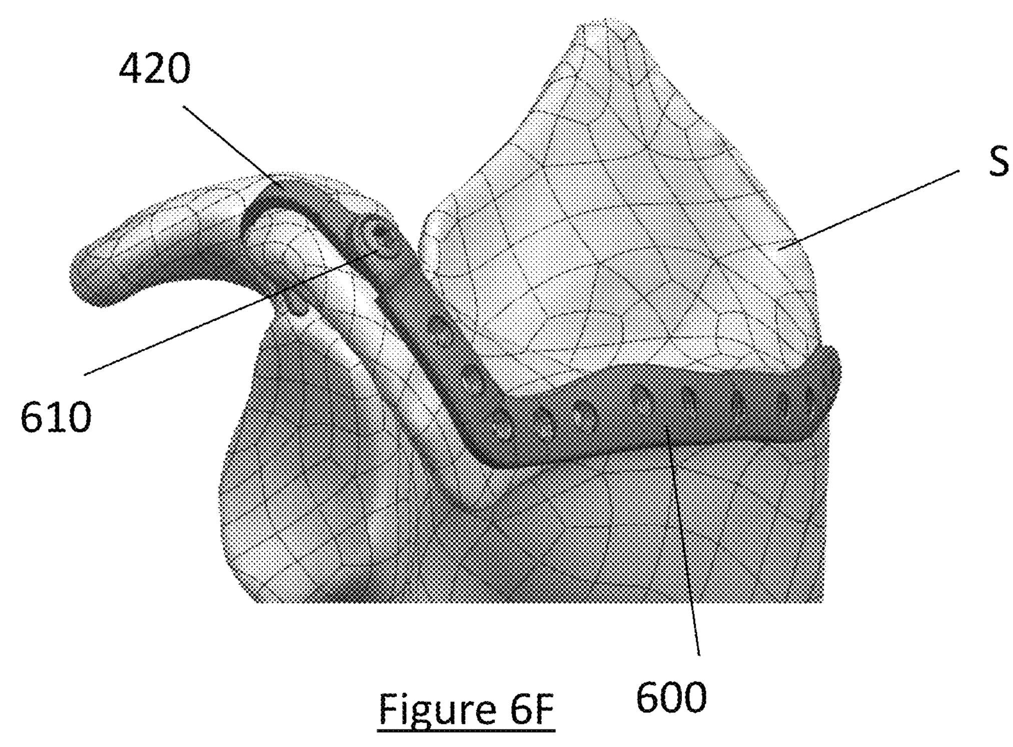
FIG. 6F shows an alternate view of the second exemplary plate and exemplary hook and representative scapula of FIG. 6E.

FIGS. 6E and 6F show perspective views of a representative scapula S, with the construct 620 secured thereto. FIG. 6E shows a posterior view and FIG. 6F shows a lateral view. As shown in FIGS. 6E and 6F, the plate 600 extends along the scapular spine and curves to extend along the acromion, and third exemplary hook 420 extends around the top of the acromion. In some embodiments, the screw 610 extends through the acromion to secure the construct 620 thereto. In some embodiments, the plate 600, the third exemplary hook 420, and the screw 610 cooperate to retain the acromion in a desired (e.g., anatomically correct) position.

Figure 7A:
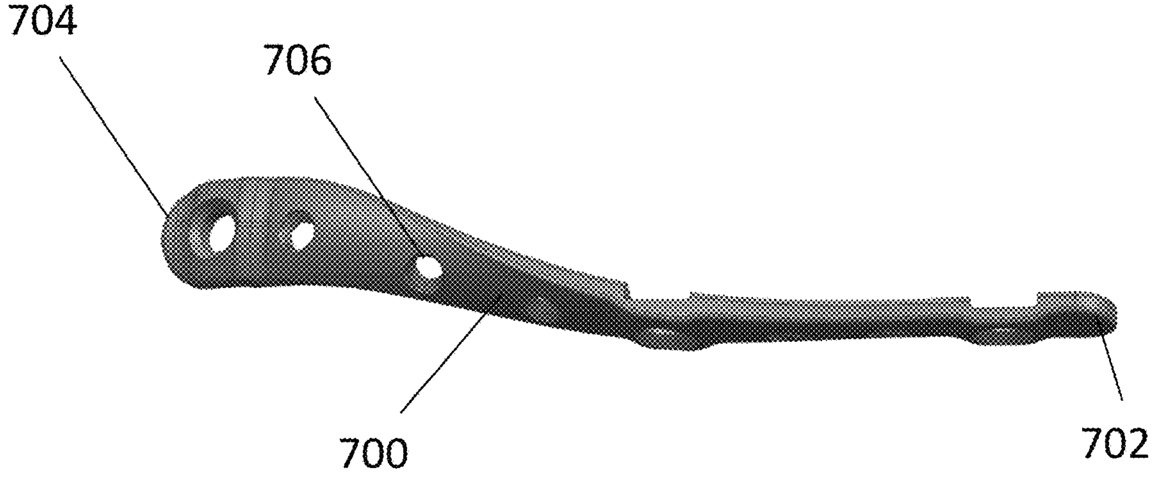
FIG. 7A shows a third exemplary plate.
Figure 7B:
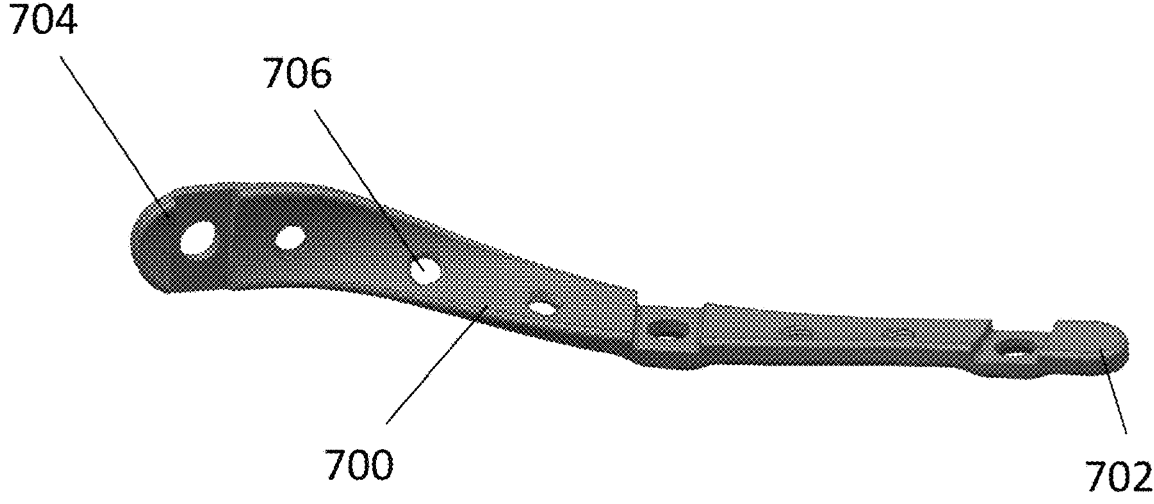
FIG. 7B shows a reverse view of the third exemplary plate of FIG. 7A.

FIGS. 7A and 7B show perspective views of a third exemplary plate 700. In some embodiments, the plate 700 is sized, shaped, and curved to extend along a scapular spine and an acromion of a patient. In some embodiments, the plate 700 includes a first end 702 (e.g., a medial end) and a second end 704 (e.g., a lateral end). In some embodiments, the plate 700 is curved such that, when the plate 700 is positioned adjacent a scapula of a patient, the first end 702 is positioned along the inferior side of the scapular spine and the second end 704 is positioned along the posterior side of the acromion. In some embodiments, the plate 700 includes a plurality of fixation points 706 (e.g., holes) extending therethrough and configured to facilitate securing the plate 700 to a bone by mechanical securing devices such as screws, sutures, wire, pins, etc. In the embodiment of the plate 700 shown in FIGS. 7A and 7B, the plate 700 includes eight (8) of the fixation points 706, but it will be apparent to those of skill in the art that this quantity is only exemplary and that the plate 700 may include any number of the fixation points 706.

Figures 7C, 7D:
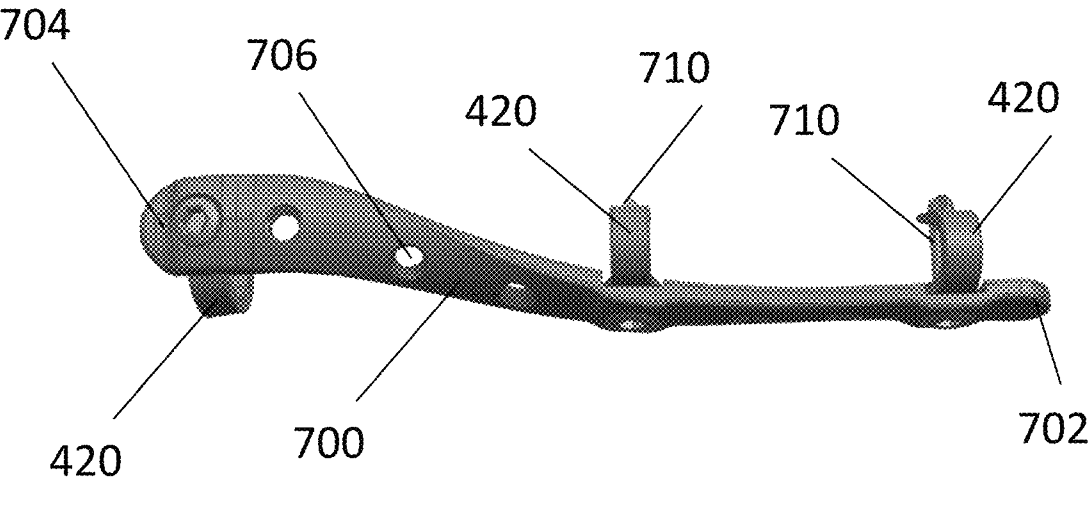
FIG. 7C shows the third exemplary plate of FIG. 7A as configured with exemplary hooks.
FIG. 7D shows an alternate view of the third exemplary plate and exemplary hooks of FIG. 7C.

FIGS. 7C and 7D show perspective views of the plate 700 as prepared for securing to a scapula of a patient. FIG. 7C shows a posterior perspective view and FIG. 7D shows an anterior perspective view. As shown in FIGS. 7C and 7D, the plate 700 has been prepared by securing a first one of the third exemplary hook 420 to the first end 702, a second one of the third exemplary hook 420 intermediate the first and second ends 702, 704, and a third one of the exemplary hook 420 to the second end 704. In some embodiments, as shown in FIGS. 7C and 7D, the third exemplary hooks 420 are secured to the plate 700 by a screw 710. The combination of the plate 700, the third exemplary hooks 420, and the screws 710 is referred to herein as a construct 720.

Figure 7E:
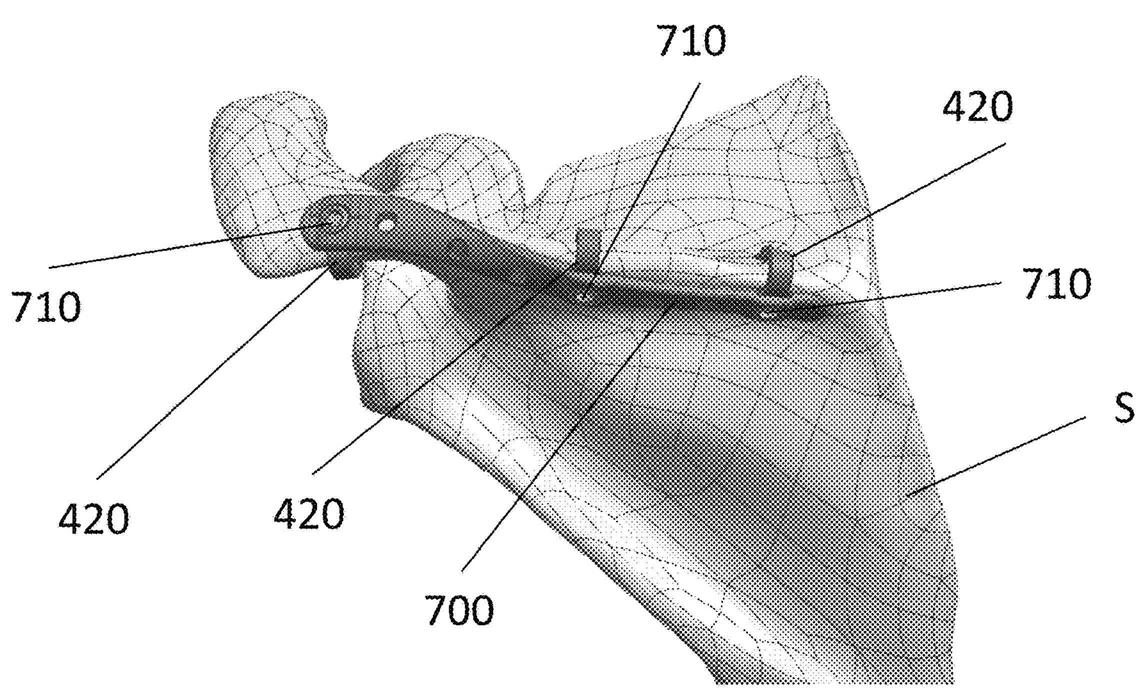
FIG. 7E shows the third exemplary plate and exemplary hooks of FIGS. 7C and 7D as secured to a representative scapula.
Figure 7F:
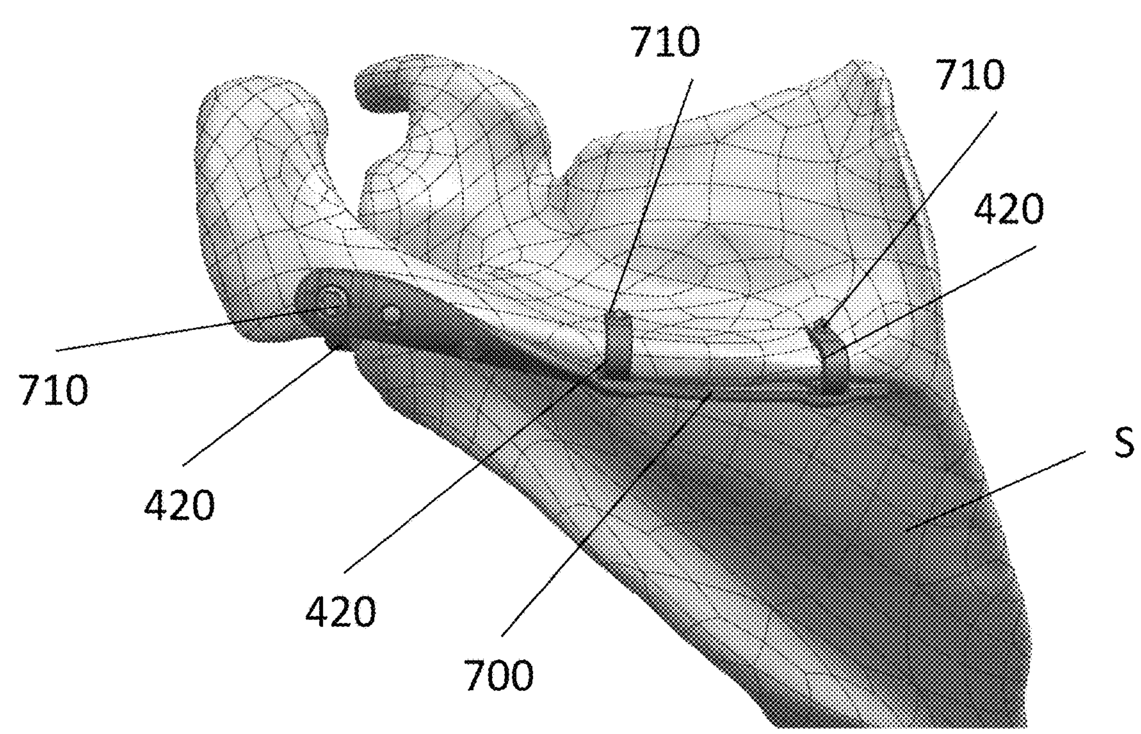
FIG. 7F shows an alternate view of the third exemplary plate and exemplary hooks and representative scapula of FIG. 7E.

FIGS. 7E and 7F show perspective views of a representative scapula S, with the construct 620 secured thereto. As shown in FIGS. 7E (posterior view) and 7F (posterior oblique view), the plate 700 extends along the inferior side of the scapular spine from the first end 702 of the plate 700 and curves to extend along the posterior of the scapular spine and the posterior of the acromion as it extends toward the second end 704 of the plate 400. The first and second ones of the third exemplary hooks 420 secure the plate 700 to the scapular spine and the third one of the exemplary hooks 420 secures the plate to the acromion. In some embodiments, the screws 710 extend through the scapular spine and the acromion to secure the construct 710 thereto. In some embodiments, the plate 700, the exemplary hooks 420, and the screws 710 cooperate to retain the acromion in a desired (e.g., anatomically correct) position.

Figure 8A:
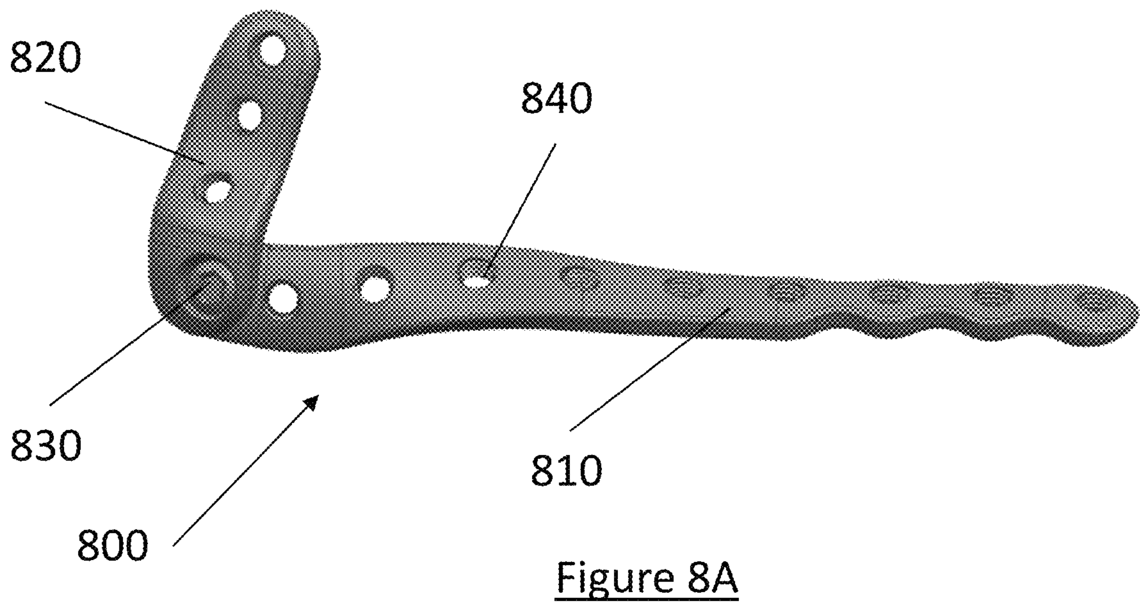
FIG. 8A shows a fourth exemplary plate that is an adjustable plate.
Figure 8B:
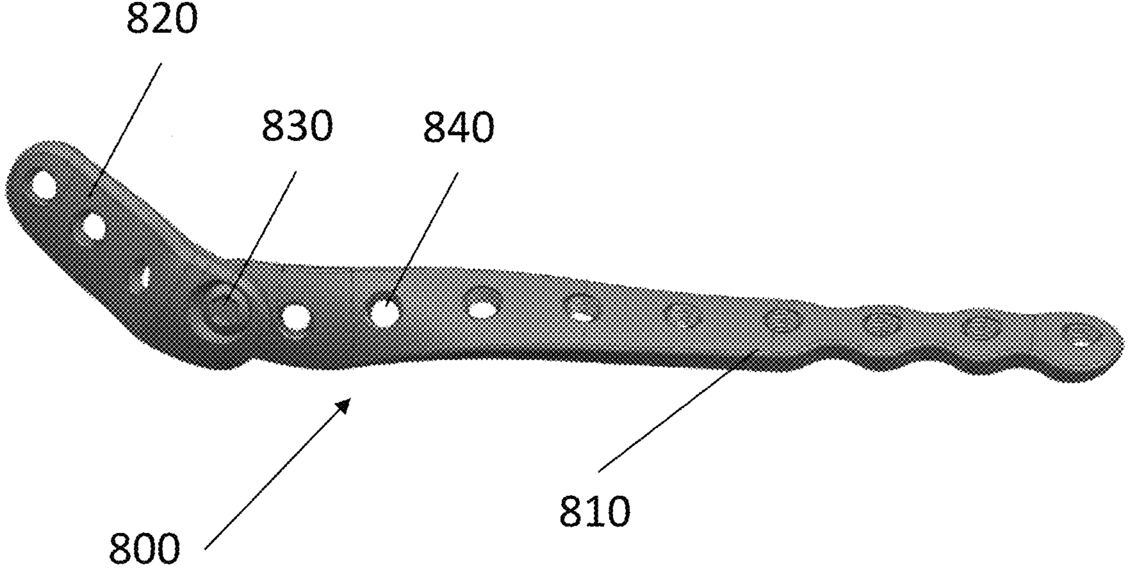
FIG. 8B shows an alternate configuration of the fourth exemplary plate of FIG. 8B.

FIGS. 8A and 8B show perspective views of a fourth exemplary plate 800. The fourth exemplary plate 800 is an adjustable plate. FIGS. 8A and 8B show the fourth exemplary plate 800 from substantially the same perspective as one another, with the plate 800 shown adjusted in a first position in FIG. 8A and in a second position in FIG. 8B. The plate 800 includes a scapular plate 810, an acromial plate 820, and a modular junction 830 connecting the acromial plate and the scapular plate. In some embodiments, the modular junction is a spherical connection that permits adjustment of the joining angle between the scapular plate 810 and the acromial plate 820, thereby to permit the position of the acromion plate 820 to be adjusted in order to account for each patient's acromial morphology and bone shape (e.g., acromial tilt). In some embodiments, the modular junction 830 can be secured/clamped, such as with a screw, thereby to fix the position of the scapular plate 810 and the acromial plate 820 with respect to one another. In some embodiments, the scapular plate 810 is sized and shaped to extend along a scapular spine of a patient. In some embodiments, the acromial plate 820 is sized and shaped to extend along an acromion spine of a patient. In some embodiments, the plate 800 includes a plurality of fixation points 840 (e.g., holes) extending therethrough and configured to facilitate securing the plate 800 to a bone by mechanical securing devices such as screws, sutures, wire, pins, etc. In the embodiment of the plate 800 shown in FIGS. 8A and 8B, the plate 800 includes twelve (12) of the fixation points 840, of which nine (9) of the fixation points 840 are located along the scapular plate 810 and three (3) of the fixation points 840 are located along the acromial plate 820, but it will be apparent to those of skill in the art that this quantity is only exemplary and that the plate 800 may include any number of the fixation points 840. In some embodiments, the plate 800 is configured to permit any of the exemplary hooks discussed herein (e.g., the first exemplary hook 400, the second exemplary hook 410, and/or the third exemplary hook 420) to be secured thereto in order to facilitate fixation to the scapula.

Figure 8C:
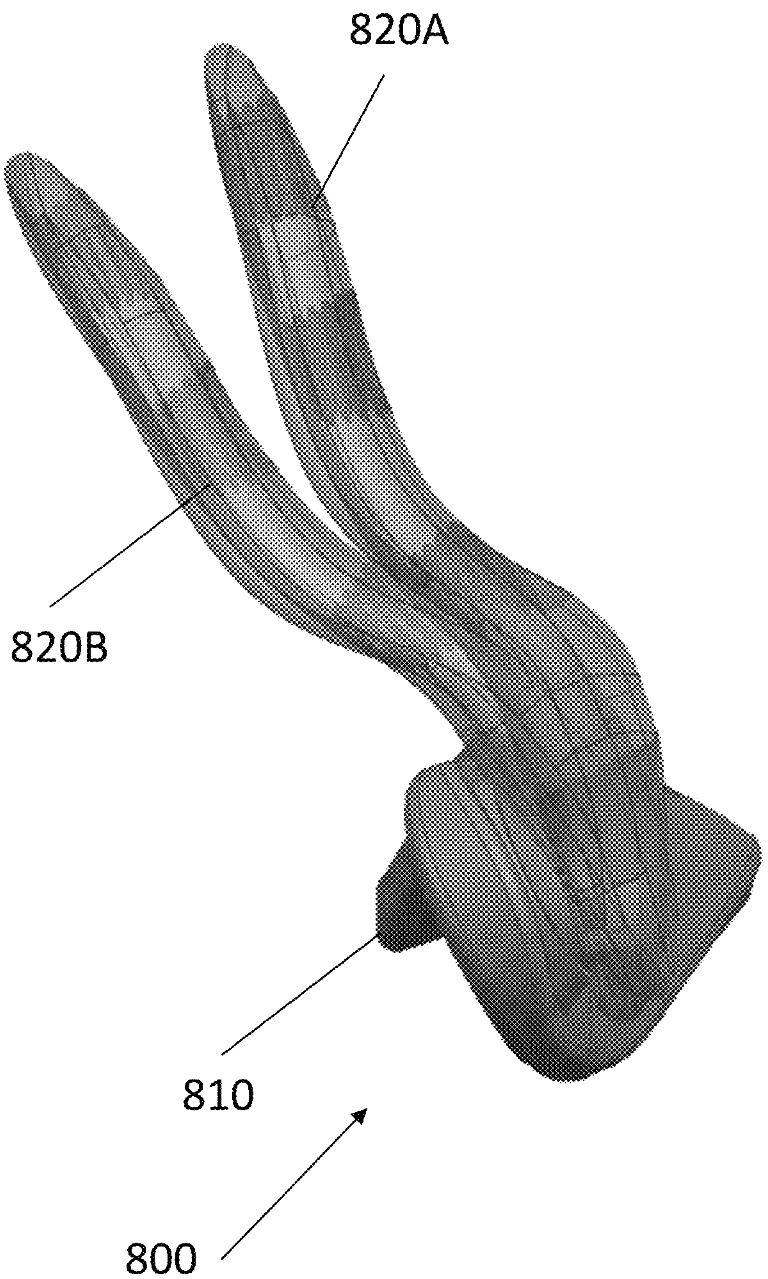
FIG. 8C shows the fourth exemplary plate of FIG. 8A with an acromial plate thereof positioned in two alternate positions.

FIG. 8C shows a lateral view of the exemplary plate 800 of FIGS. 8A and 8B. In the view of FIG. 8C, the acromial plate 820 is shown positioned in two alternate positions 820A and 820B with respect to the scapular plate 810. It may be seen from FIG. 8C that the adjustable positioning of the acromial plate 820 enables the exemplary plate 800 to be adjusted so as to properly fit patients having varying anatomy, e.g., differently angled acromions.

Figure 8D:
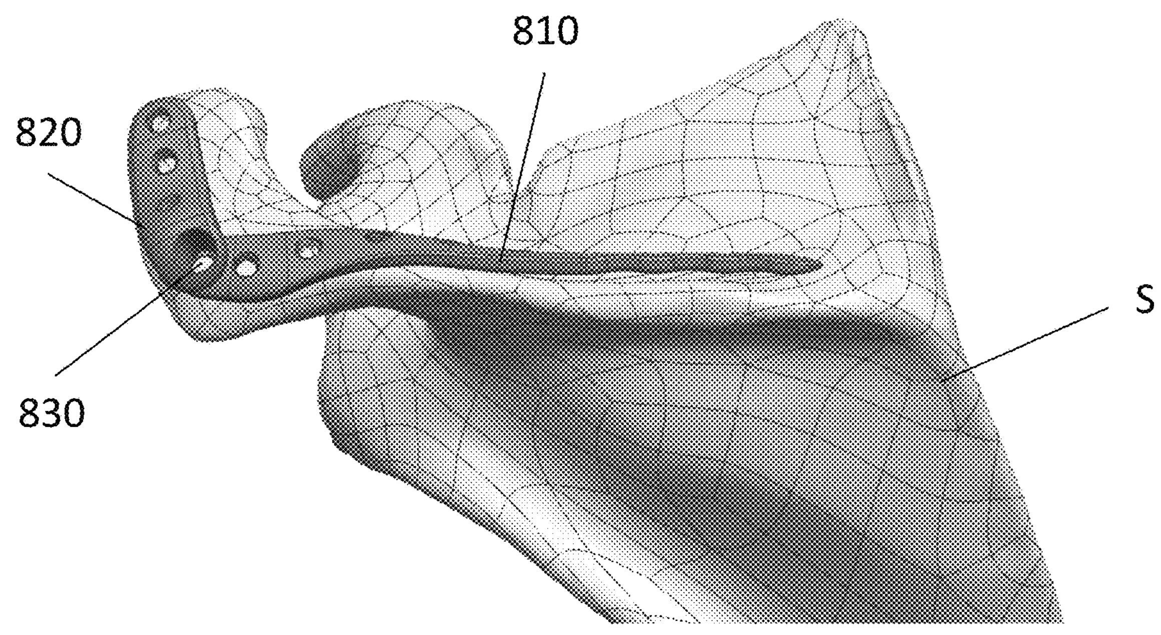
FIG. 8D shows the fourth exemplary plate of FIGS. 8A and 8B as positioned with reference to a representative scapula.
Figure 8E:
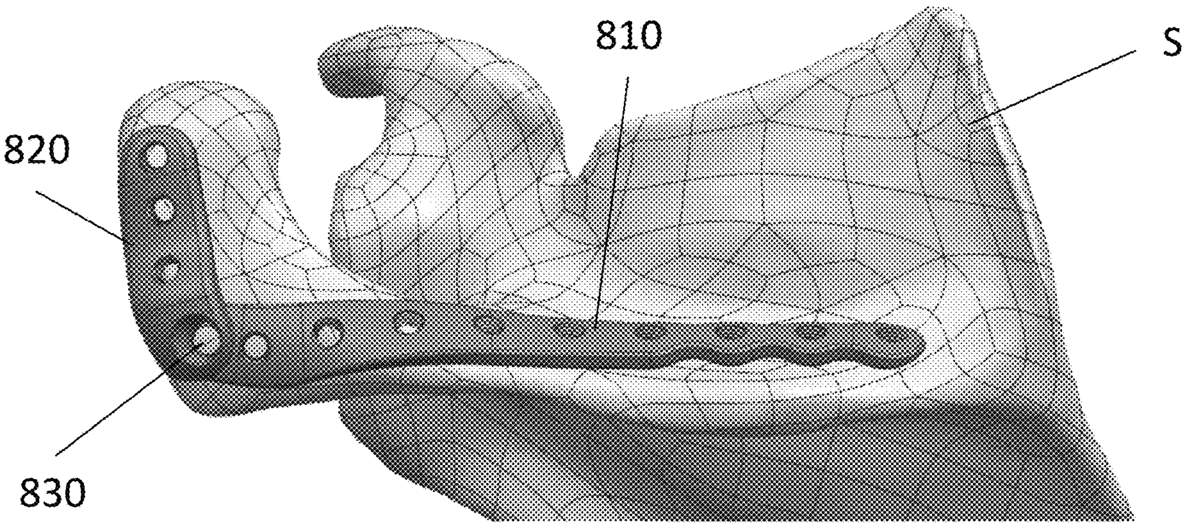
FIG. 8E shows an alternate view of the fourth exemplary plate and representative scapula of FIG. 8D.

FIGS. 8D and 8E show perspective views of a representative scapula S, with the plate 800 positioned adjacent thereto. FIGS. 8D (posterior view) and 8E (posterior oblique view) show the plate 800 in the absence of any hooks (e.g., the first exemplary hook 400, the second exemplary hook 410, and/or the third exemplary hook 420) and screws (or other similar securing mechanisms), but it will be apparent to those of skill in the art that these figures are only illustrative and that practical applications of the exemplary plate 800 may include such additional elements. As shown in FIGS. 8D and 8E, the scapular plate 810 extends along the superior side of the scapular spine, the modular junction 830 is positioned proximate the base of the acromion, and the acromial plate 820 extends along the acromion. In some embodiments, the plate 800, used in conjunction with one or more hooks (e.g., the first exemplary hook 400, the second exemplary hook 410, and/or the third exemplary hook 420)

and screws, is configured to retain the acromion in a desired (e.g., anatomically correct) position.

Figure 3C:
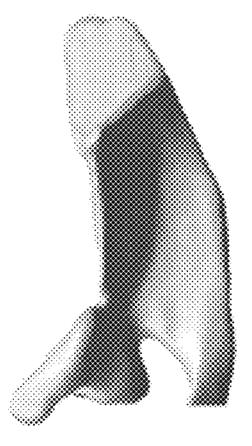
FIG. 3C shows a superior view of a scapula after a Type 1 fracture.
Figure 3D:
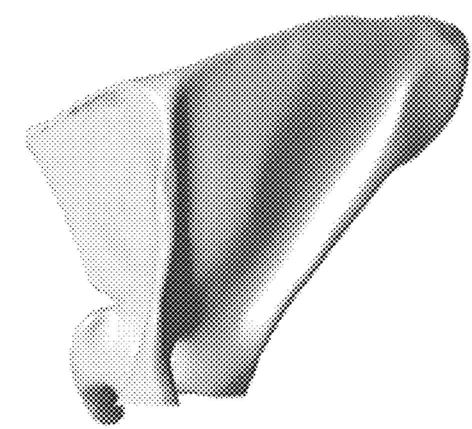
FIG. 3D shows a posterior view of the fractured scapula shown in FIG. 3C.
Figure 3A:
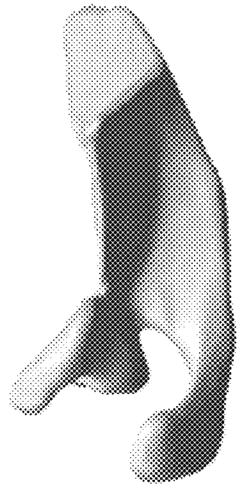
FIG. 3A shows a superior view of a healthy scapula.
Figure 3B:
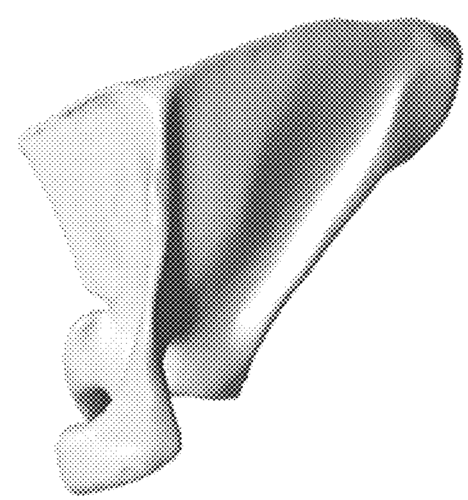
FIG. 3B shows a posterior view of the healthy scapula shown in FIG. 3A.
Figure 3G:
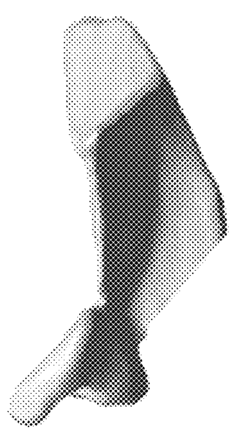
FIG. 3G shows a superior view of a scapula after a Type 3 fracture.
Figure 3H:
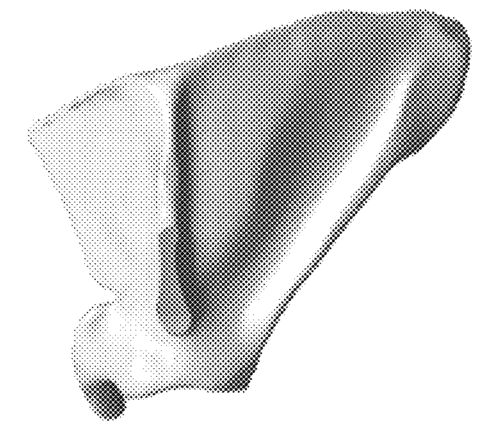
FIG. 3H shows a posterior view of the fractured scapula shown in FIG. 3G.
Figure 3E:
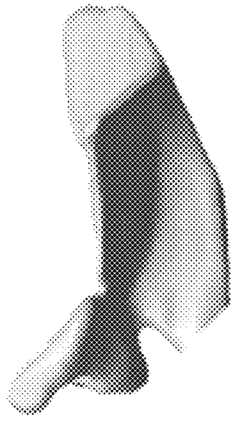
FIG. 3E shows a superior view of a scapula after a Type 2 fracture.
Figure 3F:
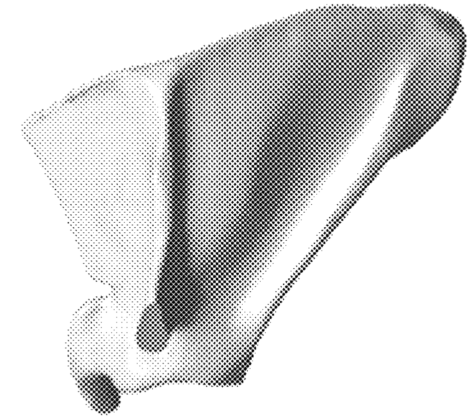
FIG. 3F shows a posterior view of the fractured scapula shown in FIG. 3E.

In some embodiments, exemplary devices are provided in multiple different sizes and shapes to account for the various fracture types that the orthopedic surgeon may be presented with. In some embodiments, exemplary devices are provided in different shapes for the different types of scapular fractures (i.e., type 1 fractures as shown in FIGS. 3C and 3D, type 2 fractures as shown in FIGS. 3E and 3F, and type 3 fractures as shown in FIGS. 3G and 3H) discussed above, each of which corresponds to a fracture at a different location within the scapula.

In some embodiments, a device includes one or more extensions or shapes to provide multiple options for screw fixation into the scapula to gain increased fixation to the native bone. In some embodiments, such extensions are integrally formed with an exemplary scapular fixation device. In some embodiments, such extensions are modularly attachable to and removable from an exemplary scapular fixation device. In some embodiments, at least one such extension is configured to provide an option for screw fixation facing the superior of the scapular spine. In some embodiments, at least one such extension is configured to provide an option for screw fixation facing the inferior of the scapular spine. In some embodiments, at least one such extension is configured to provide an option for screw fixation adjacent to the medial border to the superior of the scapular spine. In some embodiments, at least one such extension is configured to provide an option for screw fixation adjacent to the medial border to the inferior of the scapular spine.

It should be noted that each of the exemplary embodiments described herein can be secured to one or more regions of the acromion or scapular spine to provide additional strength and rigidity at the time of the initial reverse shoulder arthroplasty procedure (i.e., before a fracture occurs). By prophylactically securing such a plate to the regions of the scapula that are subjected to high stress following rTSA, the incidence of acromial and/or scapular fractures after rTSA may be reduced as any of the exemplary devices may off-load the bone and better distribute the load. In some embodiments, a strut is secured between the coracoid and/or clavicle to off-load and better distribute the loading (e.g., stress transmission) to other parts of the scapula. In practice, any of the exemplary embodiments described herein can be used individually or in combination with one another at the discretion of the orthopedic surgeon in order to best anatomically reconstruct the fractured bones and achieve fragment compression, either after the fracture occurs or prophylactically.

In some embodiments, any of the exemplary embodiments described above can be manufactured to be bendable or otherwise conformable to facilitate additional patient-specific shaping to improve initial fixation when repairing the patient's acromion and scapula. In some embodiments, the shape and contour of each of the modular hooks (e.g., the first exemplary hook 400, the second exemplary hook 410, and/or the third exemplary hook 420) can be bendable in order to better conform to the patient's scapula morphology along any of the medial, lateral, anterior, or posterior regions of the scapula. In some embodiments, sutures, tape, anchors, or screws can be used to fix the soft tissue to any of the exemplary embodiments described herein. Any of the exemplary embodiments described herein can be manufactured from different biocompatible materials, including Co—Cr, stainless steel, titanium, titanium alloys, carbon fiber reinforced polymers, ceramic, PMMA bone cement, pyrocarbon, and/or bone graft. Any of the exemplary embodiments described herein can include surface textures and/or coatings to provide additional mechanical fixation and to encourage osteo-integration. Any of the exemplary embodiments described herein can be fabricated by traditional computer aided manufacturing processes, forged, cast, injected molded, or by using additive manufacturing or similar processes. Any of the exemplary embodiments described herein can be designed based upon the patient's actual anatomy (or contra-lateral anatomy) through the use of CT reconstruction and computer modeling. Any of the exemplary embodiments described herein can be surface coated or treated with various processes to encourage fixation to the soft tissue, muscle, and/or bone.

In some embodiments, an exemplary device is formed from a metal plate that is cut and shaped to a desired size and shape. In some embodiments, the plate has a thickness in a range of between 3 mm and 10 mm. In some embodiments, the thickness is in a range of between 3 mm and 9 mm. In some embodiments, the thickness is in a range of between 3 mm and 8 mm. In some embodiments, the thickness is in a range of between 3 mm and 7 mm. In some embodiments, the thickness is in a range of between 3 mm and 6 mm. In some embodiments, the thickness is in a range of between 3 mm and 5 mm. In some embodiments, the thickness is in a range of between 3.5 mm and 4.5 mm. In some embodiments, the thickness is about 4 mm. In some embodiments, the thickness is 4 mm.

In some embodiments, the screw holes of an exemplary device have a diameter in range of between 1.0 mm and 4.5 mm. In some embodiments, the screw holes have a diameter in range of between 1.5 mm and 4.0 mm. In some embodiments, the screw holes have a diameter in range of between 2.0 mm and 3.5 mm. In some embodiments, the screw holes have a diameter in range of between 2.5 mm and 3.0 mm. In some embodiments, the screw holes have a diameter in range of between 1.0 mm and 4.0 mm. In some embodiments, the screw holes have a diameter in range of between 1.0 mm and 3.5 mm. In some embodiments, the screw holes have a diameter in range of between 1.0 mm and 3.0 mm. In some embodiments, the screw holes have a diameter in range of between 1.0 mm and 2.5 mm. In some embodiments, the screw holes have a diameter in range of between 1.0 mm and 2.0 mm. In some embodiments, the screw holes have a diameter in range of between 1.0 mm and 1.5 mm. In some embodiments, the screw holes have a diameter in range of between 1.5 mm and 4.5 mm. In some embodiments, the screw holes have a diameter in range of between 2.0 mm and 4.5 mm. In some embodiments, the screw holes have a diameter in range of between 2.5 mm and 4.5 mm. In some embodiments, the screw holes have a diameter in range of between 3.0 mm and 4.5 mm. In some embodiments, the screw holes have a diameter in range of between 3.5 mm and 4.5 mm. In some embodiments, the screw holes have a diameter in range of between 4.0 mm and 4.5 mm.

In some embodiments, in areas of the device where the screw holes are present, the screw holes may be spaced apart from one another by a spacing distance (i.e., as measured from center to center or from edge to edge). In some embodiments, the spacing distance is between 1.0 cm and 4.0 cm. In some embodiments, the spacing distance is between 1.5 cm and 3.5 cm. In some embodiments, the spacing distance is between 2.0 cm and 3.0 cm. In some embodiments, the spacing distance is between 2.5 cm and 3.5 cm. In some embodiments, the spacing distance is between 1.0 cm and 3.5 cm. In some embodiments, the spacing distance is between 1.0 cm and 3.0 cm. In some embodiments, the spacing distance is between 1.0 cm and 2.5 cm. In some embodiments, the spacing distance is between 1.0 cm and 2.0 cm. In some embodiments, the spacing distance is between 1.0 cm and 1.5 cm. In some embodiments, the spacing distance is between 1.5 cm and 4.0 cm. In some embodiments, the spacing distance is between 2.0 cm and 4.0 cm. In some embodiments, the spacing distance is between 2.5 cm and 4.0 cm. In some embodiments, the spacing distance is between 3.0 cm and 4.0 cm. In some embodiments, the spacing distance is between 3.5 cm and 4.0 cm.

Throughout the specification and claims, the following terms take the meanings explicitly associated herein, unless the context clearly dictates otherwise. The phrases "in one embodiment," "in an embodiment," and "in some embodiments"" as used herein do not necessarily refer to the same embodiment(s), though they may. Furthermore, the phrases "in another embodiment" and "in some other embodiments" as used herein do not necessarily refer to a different embodiment, although they may. Thus, as described herein, various embodiments of the invention may be readily combined, without departing from the scope or spirit of the invention.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

While a number of embodiments of the present invention have been described, it is understood that these embodiments are illustrative only, and not restrictive, and that many modifications may become apparent to those of ordinary skill in the art. For example, any dimensions discussed herein are provided as examples only, and are intended to be illustrative and not restrictive.

What is claimed is:

1. A device, comprising:

an elongate plate having a first end and a second end opposite the first end, wherein the elongate plate is sized, shaped, and curved so as to be adapted to be positioned and to extend along a scapular spine of a scapula of a patient and along an acromion of the scapula of the patient such that the first end extends toward a trigonum of the scapula and the second end is proximate to a superior end of the acromion of the scapula, wherein the elongate plate is sized and shaped so as not to include any portion that bridges an acromioclavicular joint or extends to a clavicle, and wherein the elongate plate is adapted to be secured to the scapular spine, and at least one hook, wherein the at least one hook comprises at least one of:

a first hook extending from the elongate plate in a lateral direction so as to be adapted to extend around a lateral end of the acromion when the elongate plate is secured to the scapular spine, a second hook extending from the second end of the elongate plate in a superior direction so as to be adapted to extend around a top of the acromion when the elongate plate is secured to the scapular spine, or a third hook extending from the elongate plate in a medial direction so as to be adapted to extend around the trigonum of the scapula when the elongate plate is secured to the scapular spine.

2. The device of claim 1, wherein the at least one hook comprises the first hook, and wherein the at least one hook further comprises a fourth hook extending from the elongate plate in a lateral direction so as to be adapted to extend around the lateral end of the acromion when the elongate plate is secured to the scapular spine, wherein the fourth hook is spaced apart from the first hook.

3. The device of claim 1, wherein the at least one hook is integrally formed with the elongate plate.

4. The device of claim 1, wherein the at least one hook is modular.

5. The device of claim 1, wherein the elongate plate is contoured so as to conform to the scapular spine.

6. The device of claim 1, wherein the elongate plate is conformable so as to allow a user to conform the elongate plate to a portion of the scapula.

7. The device of claim 1, wherein the elongate plate and the at least one hook are adapted to cooperate to apply a compression force to a fracture along the scapular spine when the elongate plate is secured to the scapular spine.

8. The device of claim 1, wherein the elongate plate is sized, shaped, and curved so as to be adapted to be positioned and to extend along a scapular spine such that the second end is positioned on a posterior surface of the acromion, and wherein the elongate plate is sized and shaped so as to terminate at the acromion.

9. A kit, comprising:

a device, comprising:

an elongate plate having a first end and a second end opposite the first end, wherein the elongate plate is sized, shaped, and curved so as to be adapted to be positioned and to extend along a scapular spine of a scapula of a patient and along an acromion of the scapula of the patient such that the first end extends toward a trigonum of the scapula and the second end is proximate to a superior end of the acromion of the scapula, wherein the elongate plate is sized and shaped so as not to include any portion that bridges an acromioclavicular joint or extends to a clavicle, and wherein the elongate plate comprises a plurality of fixation points extending therethrough, and at least one hook, wherein the at least one hook comprises at least one of:

a first hook extending from the elongate plate in a lateral direction so as to be adapted to extend around a lateral end of the acromion when the elongate plate is secured to the scapular spine, a second hook extending from the second end of the elongate plate in a superior direction so as to be adapted to extend around a top of the acromion when the elongate plate is secured to the scapular spine, or a third hook extending from the elongate plate in a medial direction so as to be adapted to extend around the trigonum of the scapula when the elongate plate is secured to the scapular spine; and a plurality of fasteners, wherein each of the plurality of fasteners is adapted to be fastened within one of the plurality of fixation points and secured in the scapula so as to secure the elongate plate to the scapula.

10. The kit of claim 9, wherein the at least one hook comprises the first hook, and wherein the at least one hook further comprises a fourth hook extending from the elongate plate in a lateral direction so as to be adapted to extend around the lateral end of the acromion when the elongate plate is secured to the scapular spine, wherein the fourth hook is spaced apart from the first hook.

11. The kit of claim 9, wherein the at least one hook is modular.

12. The kit of claim 9, wherein the elongate plate is contoured so as to conform to the scapular spine.

13. The kit of claim 9, wherein the elongate plate is conformable so as to allow a user to conform the elongate plate to a portion of the scapula.

14. The kit of claim 9, wherein the elongate plate and the at least one hook are adapted to cooperate to apply a compression force to a fracture along the scapular spine when the elongate plate is secured to the scapular spine.

15. A method, comprising:

(1) providing a kit comprising:

(a) a device, comprising:

an elongate plate having a first end and a second end opposite the first end, wherein the elongate plate is sized, shaped, and curved so as to be adapted to be positioned and to extend along a scapular spine of a scapula of a patient and along an acromion of the scapula of the patient such that the first end extends toward a trigonum of the scapula and the second end is proximate to a superior end of the acromion of the scapula, wherein the elongate plate is sized and shaped so as not to include any portion that bridges an acromioclavicular joint or extends to a clavicle, and wherein the elongate plate comprises a plurality of fixation points extending therethrough, and at least one hook, wherein the at least one hook comprises at least one of:

a first hook extending from the elongate plate in a lateral direction so as to be adapted to extend around a lateral end of the acromion when the elongate plate is secured to the scapular spine, or a second hook extending from the second end of the elongate plate in a superior direction so as to be adapted to extend around a top of the acromion when the elongate plate is secured to the scapular spine, or a third hook extending from the elongate plate in a medial direction so as to be adapted to extend around the trigonum of the scapula when the elongate plate is secured to the scapular spine; and (b) a plurality of fasteners, wherein each of the plurality of fasteners is adapted to be fastened within one of the plurality of fixation points and secured in the scapula so as to secure the elongate plate to the scapula;

(2) positioning the elongate plate along a scapular spine of a scapula of a patient such that the second end is proximate to an acromion of the scapula and the first end extends toward the trigonum of the scapula, wherein, if the at least one hook comprises the first hook, the positioning the elongate plate along the scapular spine of the scapula is performed such that the first hook extends around the lateral end of the acromion, wherein, if the at least one hook comprises the second hook, the positioning the elongate plate along the scapular spine of the scapula is performed such that the second hook extends around the top of the acromion, and wherein, if the at least one hook comprises the third hook, the positioning the elongate plate along the scapular spine of the scapula is performed such that the third hook extends around the trigonum of the scapula; and (3) fastening the elongate plate to the scapular spine with at least a first one of the plurality of fasteners via at least one of the plurality of fixation points of the elongate plate.

16. The method of claim 15, wherein the at least one hook comprises the first hook, and wherein the elongate plate and the first hook cooperate to apply a compression force along the scapular spine.

17. The method of claim 15, wherein the at least one hook further comprises the third hook, and wherein the elongate plate, the first hook, and the third hook cooperate to apply the compression force along the scapular spine.

18. The method of claim 15, wherein the at least one hook comprises the first hook, and wherein the at least one hook further comprises a fourth hook extending from the elongate plate in a lateral direction so as to be adapted to extend around the lateral end of the acromion when the elongate plate is secured to the scapular spine, wherein the fourth hook is spaced apart from the first hook.

19. The method of claim 15, wherein the at least one hook is modular.

20. The method of claim 15, wherein the elongate plate is contoured so as to conform to the scapular spine.

21. The method of claim 15, wherein the elongate plate is conformable so as to allow a user to conform the elongate plate to a portion of the scapula.

* * * * *